(12) United States Patent
Jenkins et al.

(10) Patent No.: US 6,645,199 B1
(45) Date of Patent: Nov. 11, 2003

(54) LOOP STRUCTURES FOR SUPPORTING DIAGNOSTIC AND THERAPEUTIC ELEMENTS CONTACT WITH BODY TISSUE AND EXPANDABLE PUSH DEVICES FOR USE WITH SAME

(75) Inventors: Thomas R. Jenkins, Oakland, CA (US); Russell B. Thompson, Los Altos, CA (US); Robert Burnside, Mountain View, CA (US); Anant V. Hegde, Newark, CA (US); David K. Swanson, Mountain View, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/447,180

(22) Filed: Nov. 22, 1999

(51) Int. Cl.[7] ................................................. A61B 18/18
(52) U.S. Cl. .............................. 606/41; 606/49; 606/50; 607/101
(58) Field of Search .................... 607/98, 99, 101–102, 607/115, 116, 119, 122; 606/41, 49, 50

(56) References Cited

U.S. PATENT DOCUMENTS

| | | | |
|---|---|---|---|
| 1,207,479 A | | 12/1916 | Bisgaard |
| 4,033,331 A | | 7/1977 | Guss et al. |
| 4,181,131 A | | 1/1980 | Ogiu |
| 4,245,624 A | | 1/1981 | Komiya |
| 4,650,466 A | | 3/1987 | Luther |
| 4,706,671 A | | 11/1987 | Weinrib |
| 4,747,405 A | * | 5/1988 | Leckrone ..................... 606/15 |
| 4,753,223 A | | 6/1988 | Bremer |
| 4,823,812 A | * | 4/1989 | Eshel et al. .............. 604/96.01 |
| 4,826,087 A | | 5/1989 | Chinery |
| 4,921,484 A | | 5/1990 | Hillstead |
| 5,041,085 A | | 8/1991 | Osborne |
| 5,098,412 A | | 3/1992 | Shiu |
| 5,156,151 A | | 10/1992 | Imran |
| 5,228,442 A | | 7/1993 | Imran |
| 5,239,999 A | | 8/1993 | Imran |
| 5,263,493 A | | 11/1993 | Avitall |
| 5,273,535 A | | 12/1993 | Edwards |
| 5,279,299 A | | 1/1994 | Imran |
| 5,306,245 A | | 4/1994 | Heavan |
| 5,327,885 A | * | 7/1994 | Griffith |
| 5,368,567 A | * | 11/1994 | Lee ............................ 604/102 |
| 5,368,592 A | | 11/1994 | Stern |

(List continued on next page.)

FOREIGN PATENT DOCUMENTS

| | | |
|---|---|---|
| DE | 3920707 A1 | 1/1991 |
| EP | 0238106 A1 | 9/1987 |
| EP | 0737487 A2 | 10/1996 |
| EP | 0868922 A2 | 10/1998 |
| EP | 0916360 A2 | 5/1999 |
| EP | 1042990 A1 | 10/2000 |
| WO | WO95/10253 | 4/1995 |
| WO | WO96/0042 | 1/1996 |
| WO | WO96/00042 | 1/1996 |
| WO | WO97/17892 | 5/1997 |
| WO | WO97/37607 | 10/1997 |
| WO | WO97/42966 | 11/1997 |
| WO | WO98/26724 | 6/1998 |
| WO | WO99/02096 | 1/1999 |
| WO | WO99/18878 | 4/1999 |
| WO | WO99/34741 | 7/1999 |
| WO | WO00/01313 | 1/2000 |

OTHER PUBLICATIONS

U.S. Pat. Pub. No. 2001/007070 A1, dated Jul. 5, 2001.

*Primary Examiner*—Roy D. Gibson
(74) *Attorney, Agent, or Firm*—Henricks, Slavin & Holmes LLP

(57) ABSTRACT

An apparatus that facilitates the creation of circumferential lesions in body tissue. The apparatus includes a first probe having a loop structure that supports electrodes or other operative elements against the body tissue and a second probe with an expandable push structure that may be used to urge the loop structure against body tissue.

34 Claims, 13 Drawing Sheets

U.S. PATENT DOCUMENTS

| | | |
|---|---|---|
| 5,370,675 A | 12/1994 | Edwards |
| 5,399,165 A | 3/1995 | Paul, Jr. |
| 5,415,656 A | 5/1995 | Tohon et al. |
| 5,437,665 A | 8/1995 | Munro |
| 5,439,006 A | 8/1995 | Brennen |
| 5,456,667 A | 10/1995 | Ham |
| 5,482,037 A | 1/1996 | Borghi |
| 5,487,385 A | 1/1996 | Avitall |
| 5,487,757 A | 1/1996 | Truckai |
| 5,500,012 A | 3/1996 | Brucker |
| 5,549,661 A | 8/1996 | Kordis |
| 5,571,038 A | 11/1996 | Lennox |
| 5,582,609 A | 12/1996 | Swanson |
| 5,595,183 A * | 1/1997 | Swanson et al. |
| 5,637,090 A | 6/1997 | McGee |
| 5,672,174 A | 9/1997 | Gough |
| 5,702,365 A * | 12/1997 | King .......................... 604/105 |
| 5,702,368 A | 12/1997 | Stevens |
| 5,702,438 A | 12/1997 | Avitall |
| 5,709,224 A | 1/1998 | Behl |
| 5,716,325 A * | 2/1998 | Bonutti ...................... 600/153 |
| 5,722,401 A | 3/1998 | Pietroski |
| 5,730,127 A | 3/1998 | Avitall |
| 5,738,683 A | 4/1998 | Osypka |
| 5,782,239 A * | 7/1998 | Webster et al. |
| 5,782,899 A * | 7/1998 | Imran ......................... 607/122 |
| 5,800,482 A | 9/1998 | Pomeranz |
| 5,800,484 A | 9/1998 | Gough |
| 5,820,591 A | 10/1998 | Thompson |
| 5,830,213 A | 11/1998 | Panescu |
| 5,836,947 A | 11/1998 | Fleischman |
| 5,860,974 A | 1/1999 | Abele |
| 5,863,291 A | 1/1999 | Schaer |
| 5,865,800 A | 2/1999 | Mirarchi |
| 5,879,295 A | 3/1999 | Li |
| 5,895,417 A | 4/1999 | Pomeranz |
| 5,910,129 A | 6/1999 | Koblish |
| 5,931,811 A | 8/1999 | Haissaguerre |
| 5,938,660 A | 8/1999 | Swartz |
| 5,971,983 A | 10/1999 | Lesh |
| 5,972,019 A | 10/1999 | Engelson et al. |
| 6,012,457 A | 1/2000 | Lesh |
| 6,013,052 A | 1/2000 | Durman |
| 6,016,811 A | 1/2000 | Knopp |
| 6,024,740 A | 2/2000 | Lesh |
| 6,027,473 A | 2/2000 | Ponzi |
| 6,029,671 A | 2/2000 | Stevens |
| 6,048,329 A | 4/2000 | Thompson |
| 6,064,902 A | 5/2000 | Haissaguerre |
| 6,066,100 A * | 5/2000 | Willard et al. .............. 600/452 |
| 6,071,271 A | 6/2000 | Baker et al. |
| 6,071,274 A | 6/2000 | Thompson |
| 6,071,279 A | 6/2000 | Whayne |
| 6,086,581 A | 7/2000 | Reynolds |
| 6,117,101 A | 9/2000 | Diederich |
| 6,117,154 A * | 9/2000 | Barbut et al. ............... 606/181 |
| 6,120,500 A | 9/2000 | Bednarek |
| 6,152,899 A * | 11/2000 | Farley et al. ............... 604/113 |
| 6,164,283 A | 12/2000 | Lesh |
| 6,179,835 B1 * | 1/2001 | Panescu et al. .............. 606/41 |
| 6,203,525 B1 | 3/2001 | Whayne |
| 6,214,002 B1 | 4/2001 | Fleischman |
| 6,251,093 B1 * | 6/2001 | Valley et al. ................. 604/96 |
| 6,325,797 B1 | 12/2001 | Stewart |
| 6,402,746 B1 | 6/2002 | Whayne |
| 6,413,234 B1 | 7/2002 | Thompson |
| 6,454,758 B1 | 9/2002 | Thompson |
| 6,464,700 B1 | 10/2002 | Koblish |
| 6,529,756 B1 | 3/2003 | Phan |
| 6,542,781 B1 | 4/2003 | Koblish |

\* cited by examiner

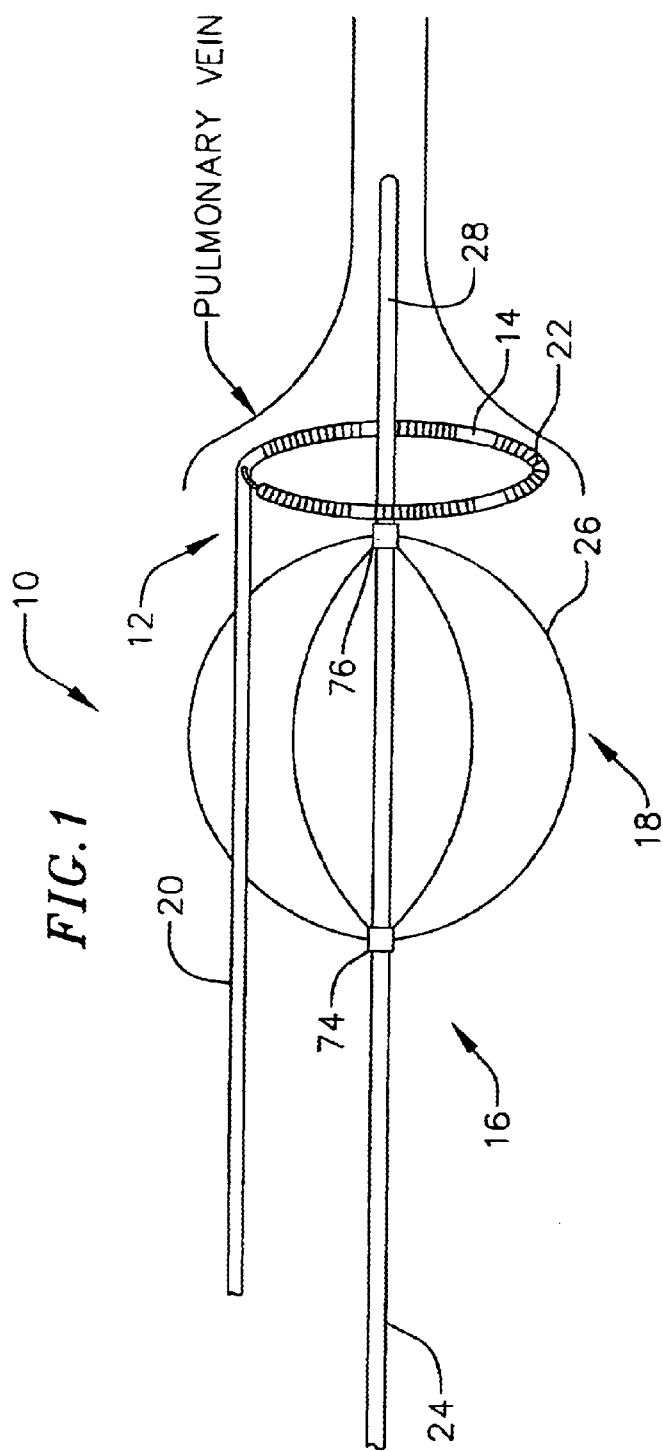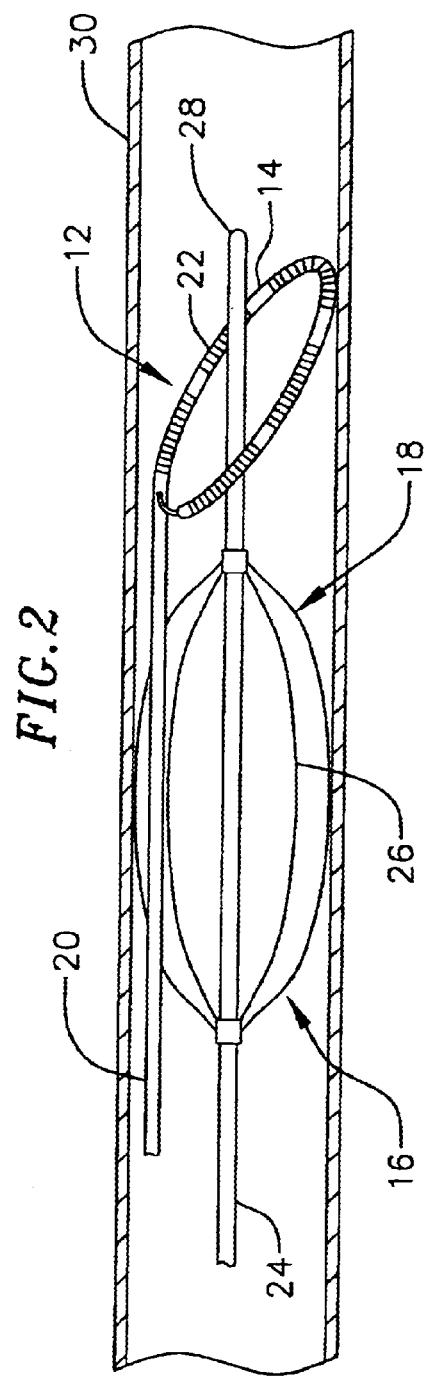

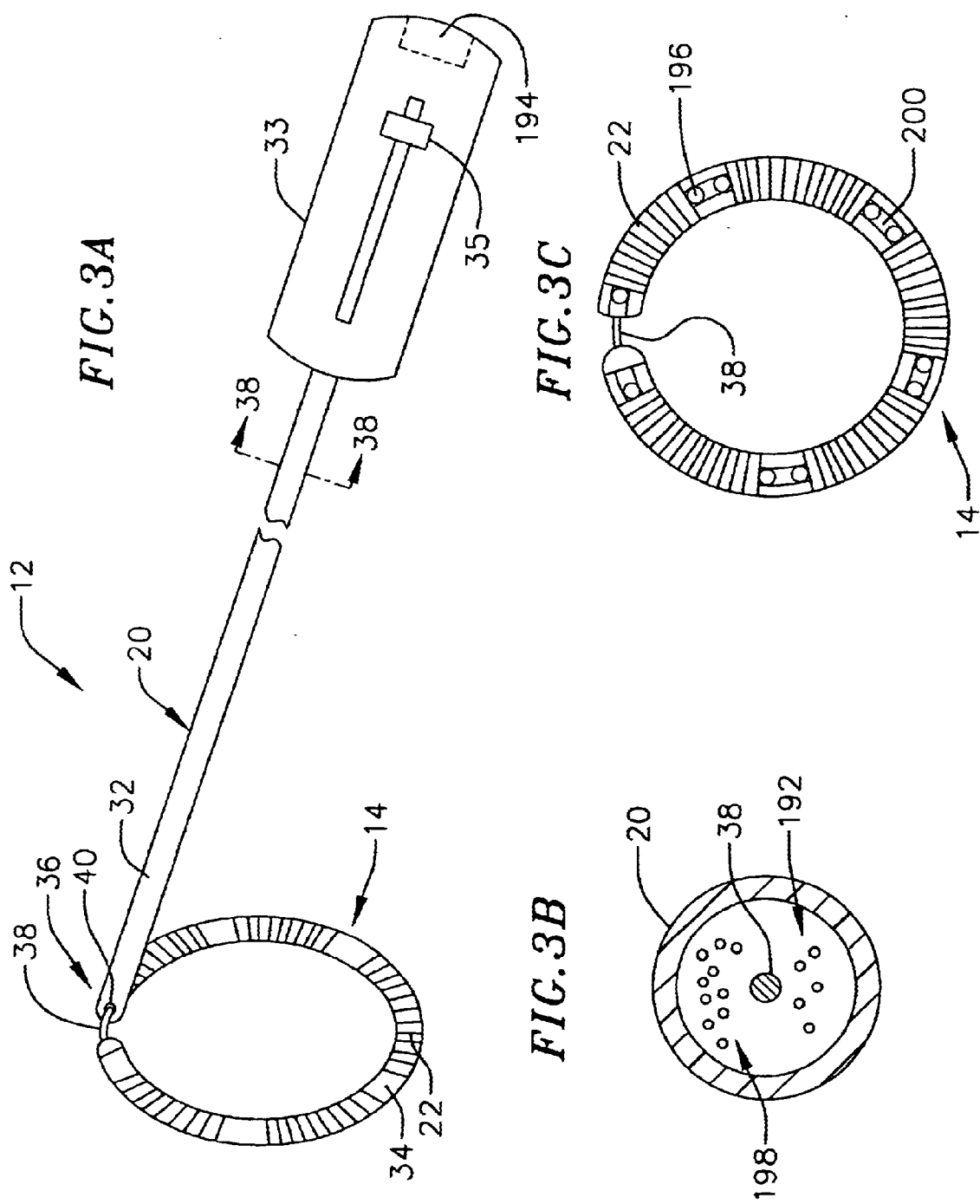

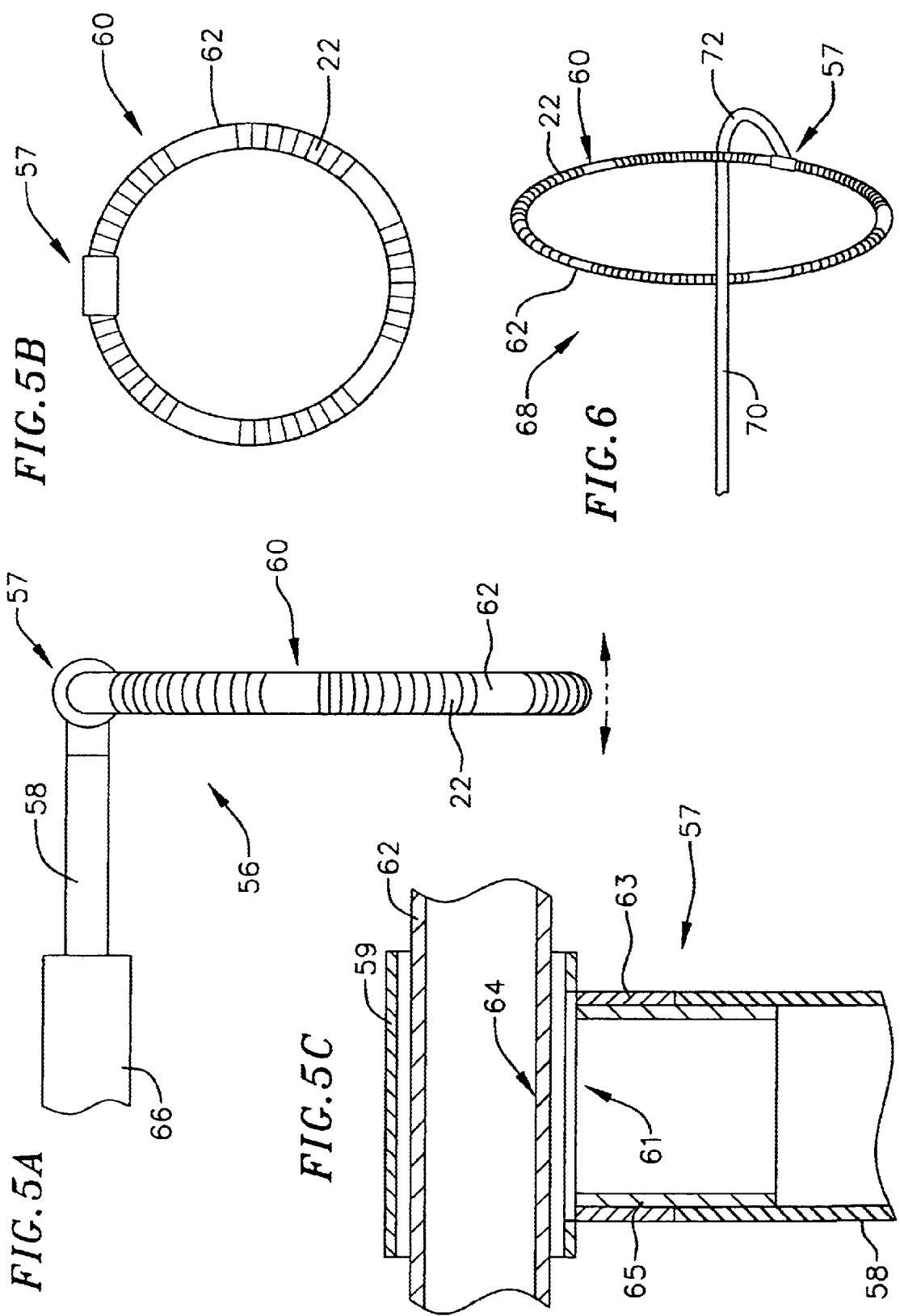

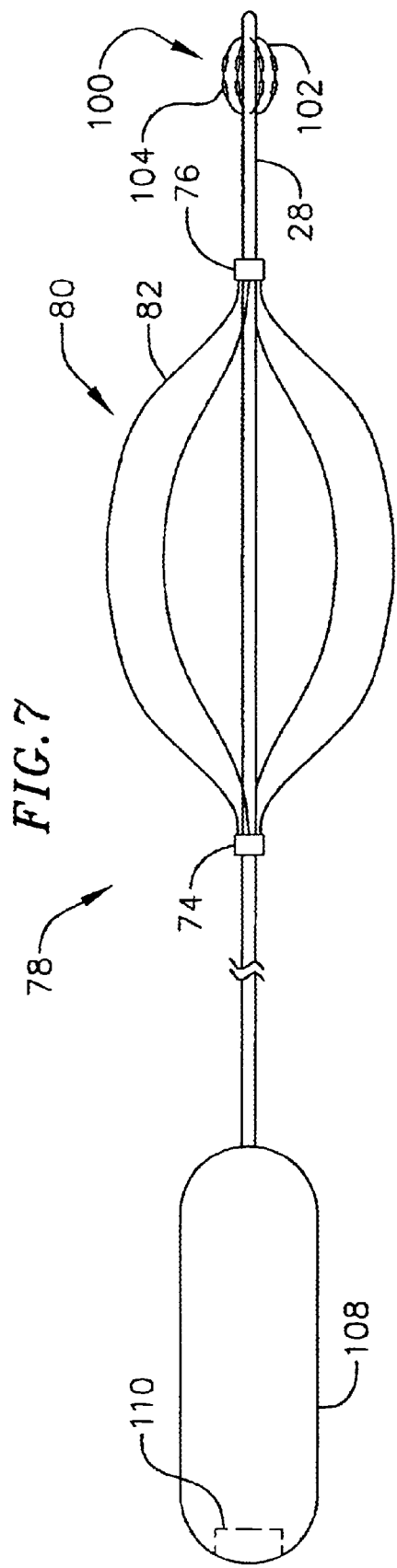
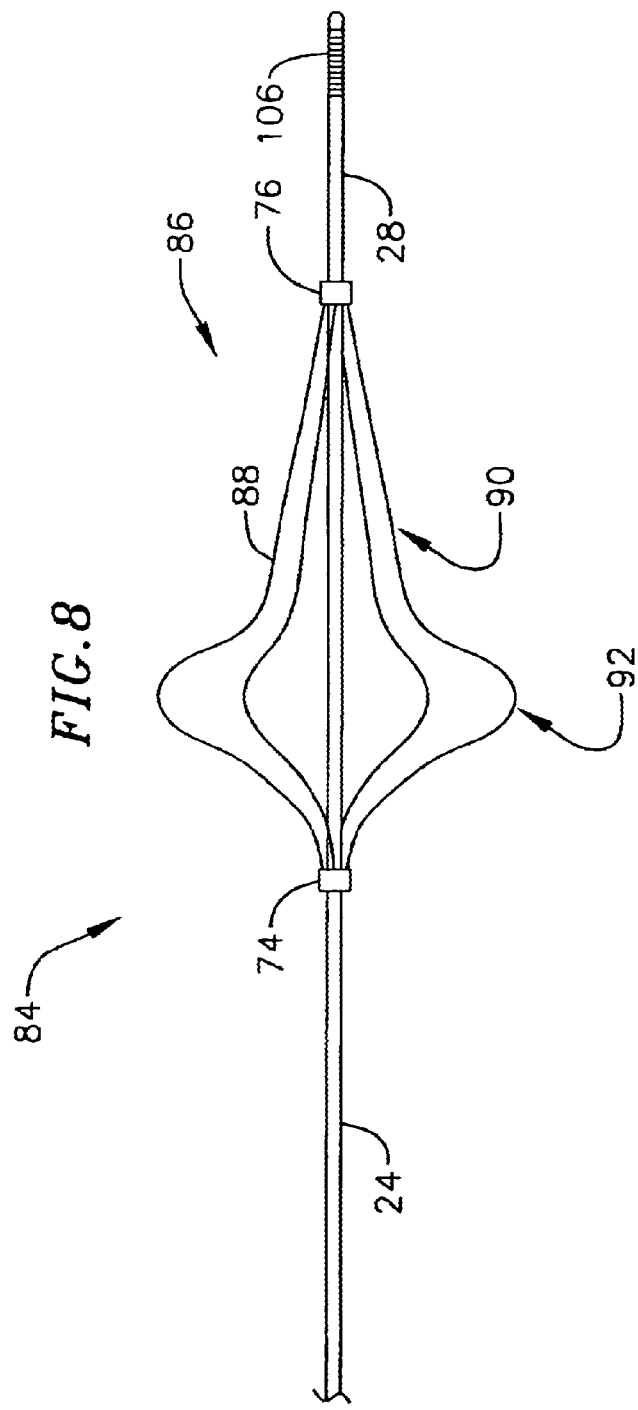

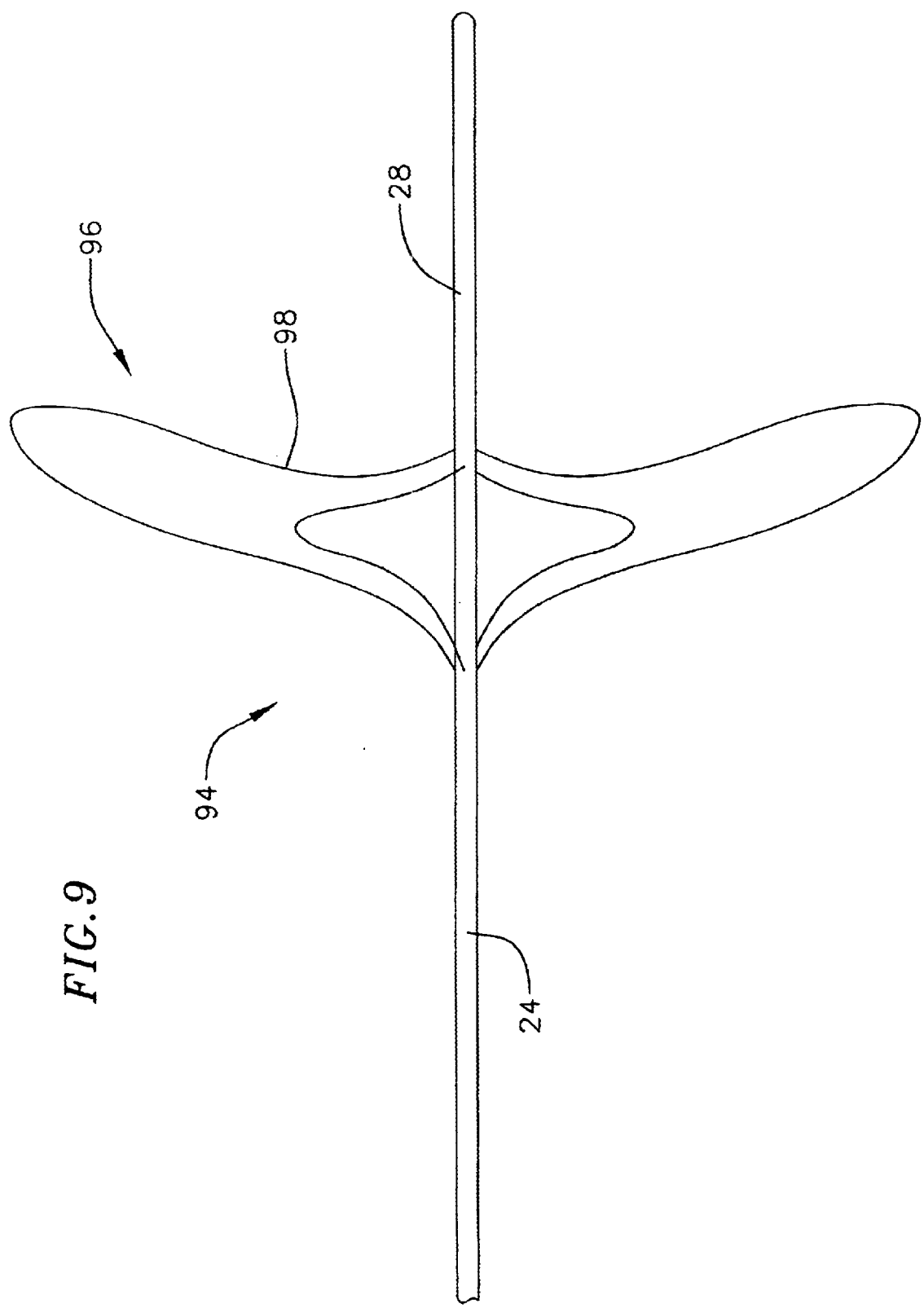

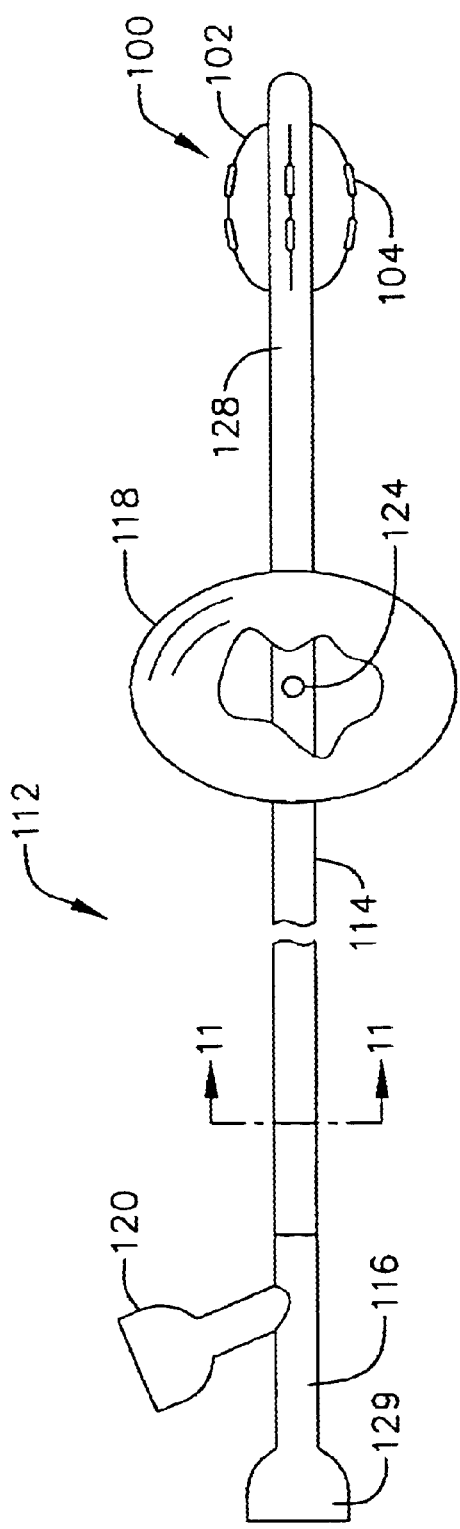
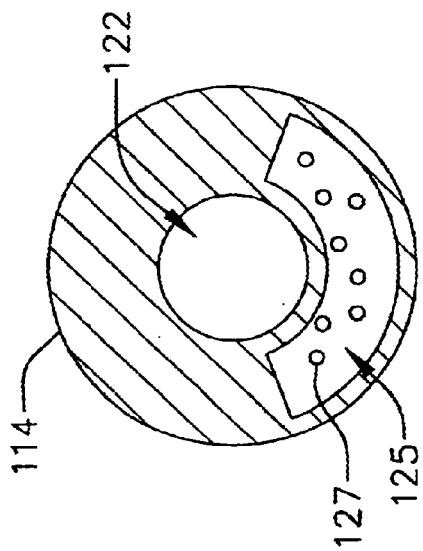
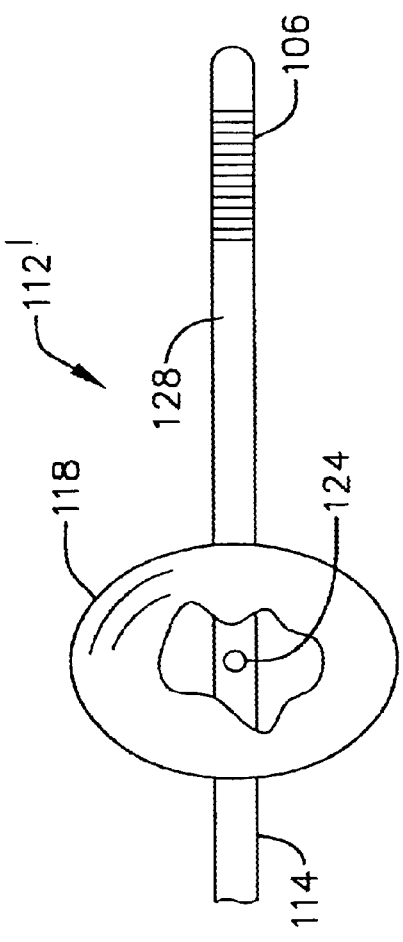

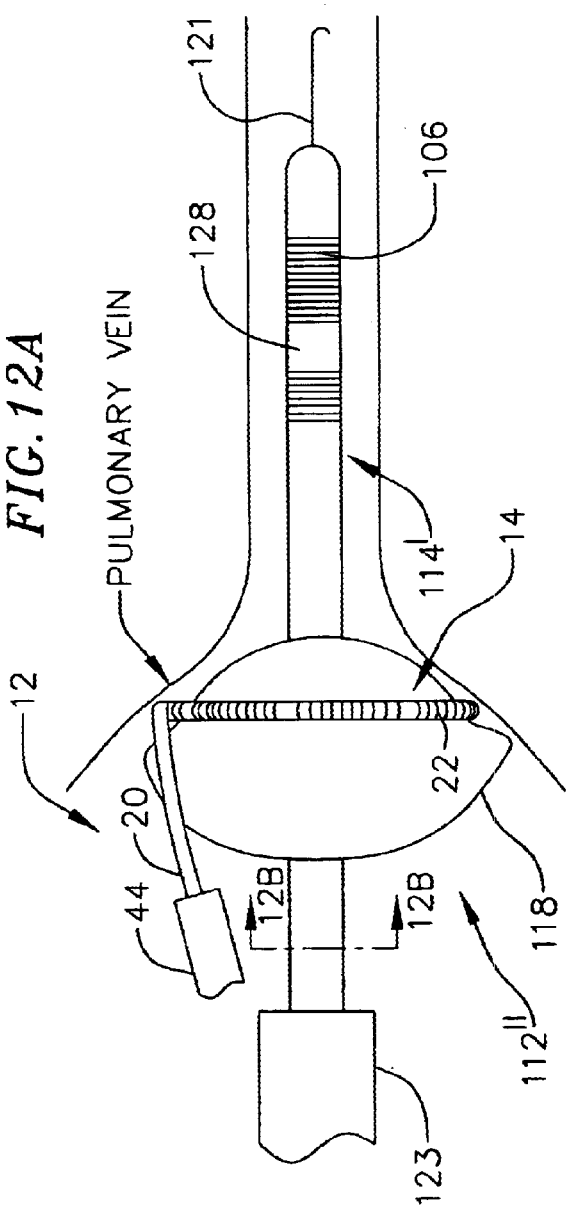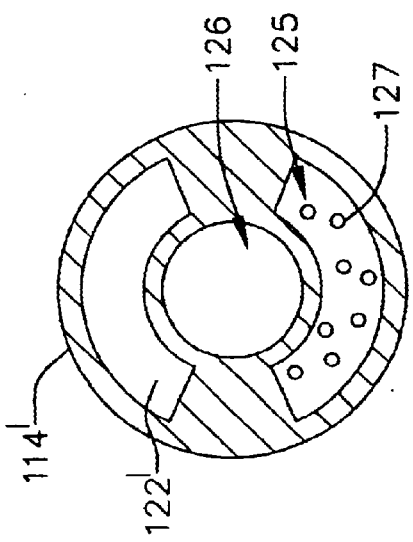

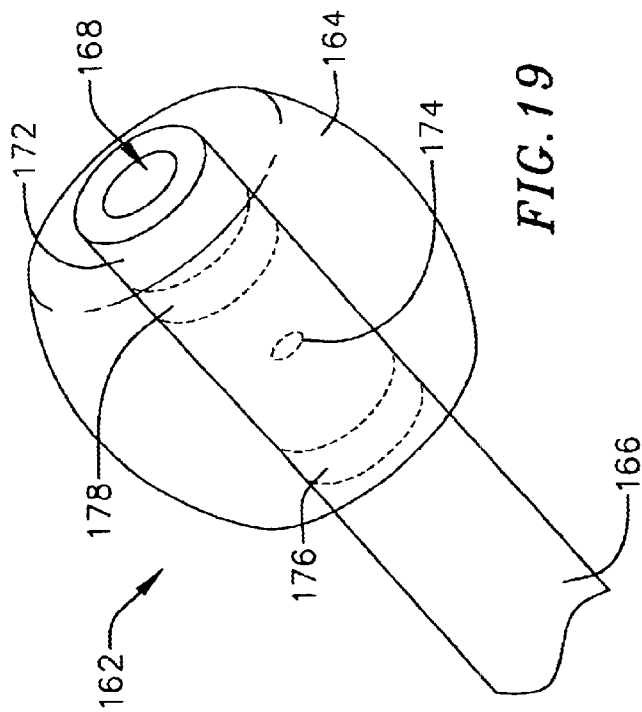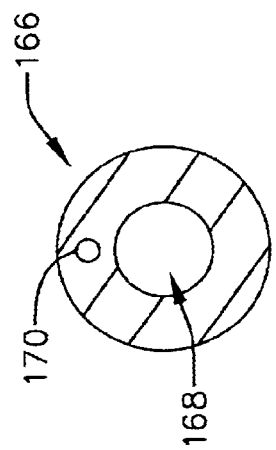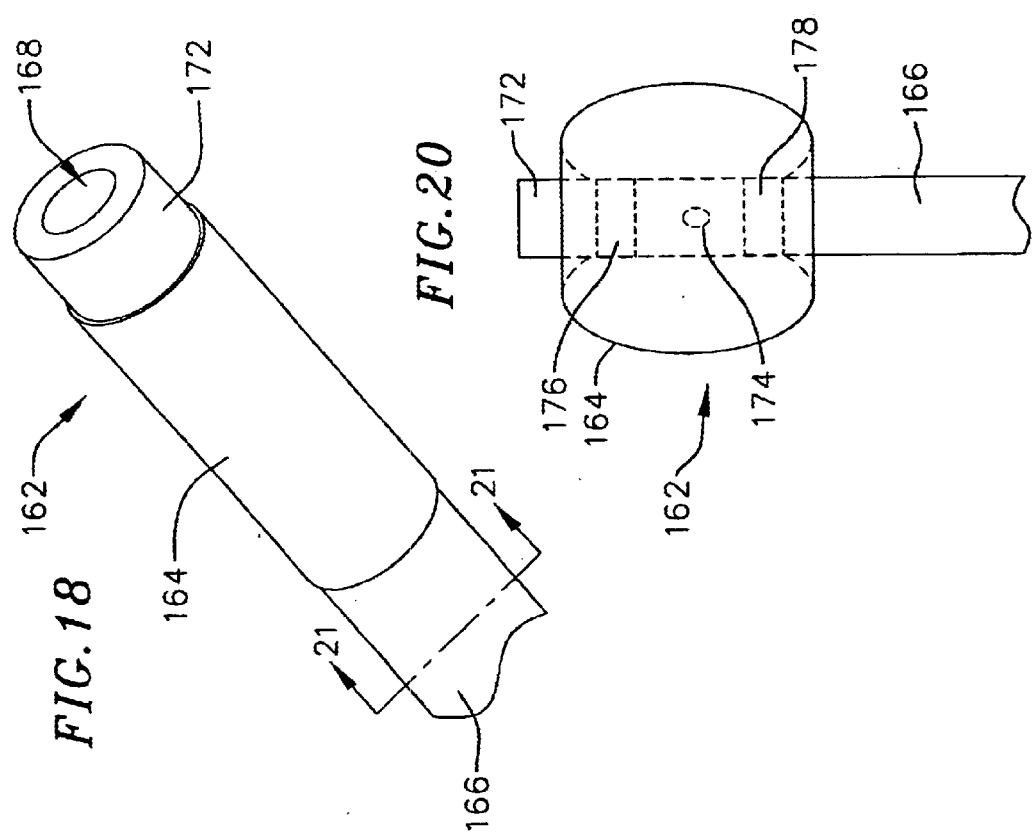

LOOP STRUCTURES FOR SUPPORTING DIAGNOSTIC AND THERAPEUTIC ELEMENTS CONTACT WITH BODY TISSUE AND EXPANDABLE PUSH DEVICES FOR USE WITH SAME

BACKGROUND OF THE INVENTIONS

1. Field of Inventions

The present inventions relate generally to medical devices that support one or more diagnostic or therapeutic elements in contact with body tissue and, more particularly, to medical devices that support one or more diagnostic or therapeutic elements in contact with bodily orifices or the tissue surrounding such orifices.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive.

Maze-like procedures have also been developed utilizing catheters which can form lesions on the endocardium (the lesions being 1 to 15 cm in length and of varying shape) to effectively create a maze for electrical conduction in a predetermined path. The formation of these lesions by soft tissue coagulation (also referred to as "ablation") can provide the same therapeutic benefits that the complex incision patterns that the surgical maze procedure presently provides, but without invasive, open heart surgery.

Catheters used to create lesions typically include a relatively long and relatively flexible body portion that has a soft tissue coagulation electrode on its distal end and/or a series of spaced tissue coagulation electrodes near the distal end. The portion of the catheter body portion that is inserted into the patient is typically from 23 to 55 inches in length and there may be another 8 to 15 inches, including a handle, outside the patient. The length and flexibility of the catheter body allow the catheter to be inserted into a main vein or artery (typically the femoral artery), directed into the interior of the heart, and then manipulated such that the coagulation electrode contacts the tissue that is to be ablated. Fluoroscopic imaging is used to provide the physician with a visual indication of the location of the catheter.

In some instances, the proximal end of the catheter body is connected to a handle that includes steering controls. Exemplary catheters of this type are disclosed in U.S. Pat. No. 5,582,609. In other instances, the catheter body is inserted into the patient through a sheath and the distal portion of the catheter is bent into loop that extends outwardly from the sheath. This may be accomplished by pivotably securing the distal end of the catheter to the distal end of the sheath, as is illustrated in co-pending U.S. application Ser. No. 08/769,856, filed Dec. 19, 1996, and entitled "Loop Structures for Supporting Multiple Electrode Elements," which is incorporated herein by reference. The loop is formed as the catheter is pushed in the distal direction. The loop may also be formed by securing a pull wire to the distal end of the catheter that extends back through the sheath, as is illustrated in U.S. Pat. No. 5,910,129, which is incorporated herein by reference. Loop catheters are advantageous in that they tend to conform to different tissue contours and geometries and provide intimate contact between the spaced tissue coagulation electrodes (or other diagnostic or therapeutic elements) and the tissue.

One lesion that has proven to be difficult to form with conventional devices is the circumferential lesion that is used to isolate the pulmonary vein and cure ectopic atrial fibrillation. Lesions that isolate the pulmonary vein may be formed within the pulmonary vein itself or in the tissue surrounding the pulmonary vein. Conventional steerable catheters and loop catheters have proven to be less than effective with respect to the formation of such circumferential lesions. Specifically, it is difficult to form an effective circumferential lesion by forming a pattern of relatively small diameter lesions. It is also difficult to attain a sufficient level of tissue contact sufficient to create a curative lesion with conventional steerable and loop catheters.

Accordingly, the inventors herein have determined that a need exists generally for structures that can be used to create circumferential lesions within or around bodily orifices and, in the context of the treatment of atrial fibrillation, within or around the pulmonary vein. The inventors herein have also determined that a need exists for an apparatus including a loop structure that attains a level of tissue contact sufficient to create curative lesions.

SUMMARY OF THE INVENTION

Accordingly, the general object of the present inventions is to provide an apparatus that avoids, for practical purposes, the aforementioned problems. In particular, one object of the present inventions is to provide an apparatus that can be used to create circumferential lesions in or around the pulmonary vein and other bodily orifices in a more efficient manner than conventional apparatus. Another object of the present inventions is to provide an apparatus including a loop structure that attains a superior level of tissue contact.

In order to accomplish some of these and other objectives, an apparatus in accordance with one embodiment of a present invention includes a first probe including a loop structure, at least one operative element associated with the loop structure, and a second probe including an expandable push structure. The loop structure may, for example, be located adjacent the pulmonary vein and the push structure may be used to urge the loop structure against the tissue. The present invention thereby eliminates the tissue contact problems associated with conventional steerable and loop catheters and allows curative lesions to be quickly and efficiently formed.

In order to accomplish some of these and other objectives, a sheath in accordance with one embodiment of a present invention includes an elongate body defining a probe lumen, a distal opening and an expandable push structure. Such a sheath performs at least two important functions. A therapeutic device, such as a probe including an operative element supporting loop structure, may be advanced through the probe lumen to the tissue region of interest. The expandable push structure may then be used to urge the therapeutic device against the tissue so that a satisfactory level of tissue contact is attained. Here too, the present invention thereby eliminates the tissue contact problems associated with conventional steerable and loop catheters and allows curative lesions to be quickly and efficiently formed.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 1 is a side view of an apparatus including a probe having a loop structure and a probe having an expandable push structure in accordance with a preferred embodiment of a present invention.

FIG. 2 is a side, partial section view of the apparatus illustrated in FIG. 1 positioned within a sheath.

FIG. 3A is a perspective view of a probe including a loop structure in accordance with a preferred embodiment of a present invention.

FIG. 3B is a section view taken along line 3B—3B in FIG. 3A.

FIG. 3C is an end view of the loop structure illustrated in FIG. 3A.

FIG. 5A is a side view of a still another probe including a loop structure in accordance with a preferred embodiment of a present invention.

FIG. 5B is an end view of the probe illustrated in FIG. 5A.

FIG. 5C is a section view of a portion of the probe illustrated in FIG. 5A.

FIG. 6 is a perspective view of yet another probe including a loop structure in accordance with a preferred embodiment of a present invention.

FIG. 7 is a side view of a probe including a basket-type expandable push structure in accordance with a preferred embodiment of a present invention.

FIG. 8 is a side view of another probe including a basket-type expandable push structure in accordance with a preferred embodiment of a present invention.

FIG. 9 is a side view of still another probe including a basket-type expandable push structure in accordance with a preferred embodiment of a present invention.

FIG. 10A is a side view of a probe including an inflatable-type expandable push structure in accordance with a preferred embodiment of a present invention.

FIG. 10B is a partial side view of another probe including an inflatable-type expandable push structure in accordance with a preferred embodiment of a present invention.

FIG. 11 is a section view of a catheter body taken along line 11—11 in FIG. 10A.

FIG. 12A is a side view of an apparatus including a probe having a loop structure and still another probe including an inflatable-type expandable push structure in accordance with a preferred embodiment of a present invention.

FIG. 12B is a section is view of a catheter body taken along line 12B—12B in FIG. 12A.

FIG. 18 is a partial perspective view of a sheath including an inflatable-type expandable push structure in an unexpanded state in accordance with a preferred embodiment of a present invention.

FIG. 19 is a partial perspective view of the sheath illustrated in FIG. 18 with the push structure in an expanded state.

FIG. 20 is a side view of the sheath illustrated in FIG. 19.

FIG. 21 is a section view taken along line 21—21 in FIG. 18.

DETAILED DESCRIPTION OF THE PREFERRED EMBODIMENTS

Figure 4:
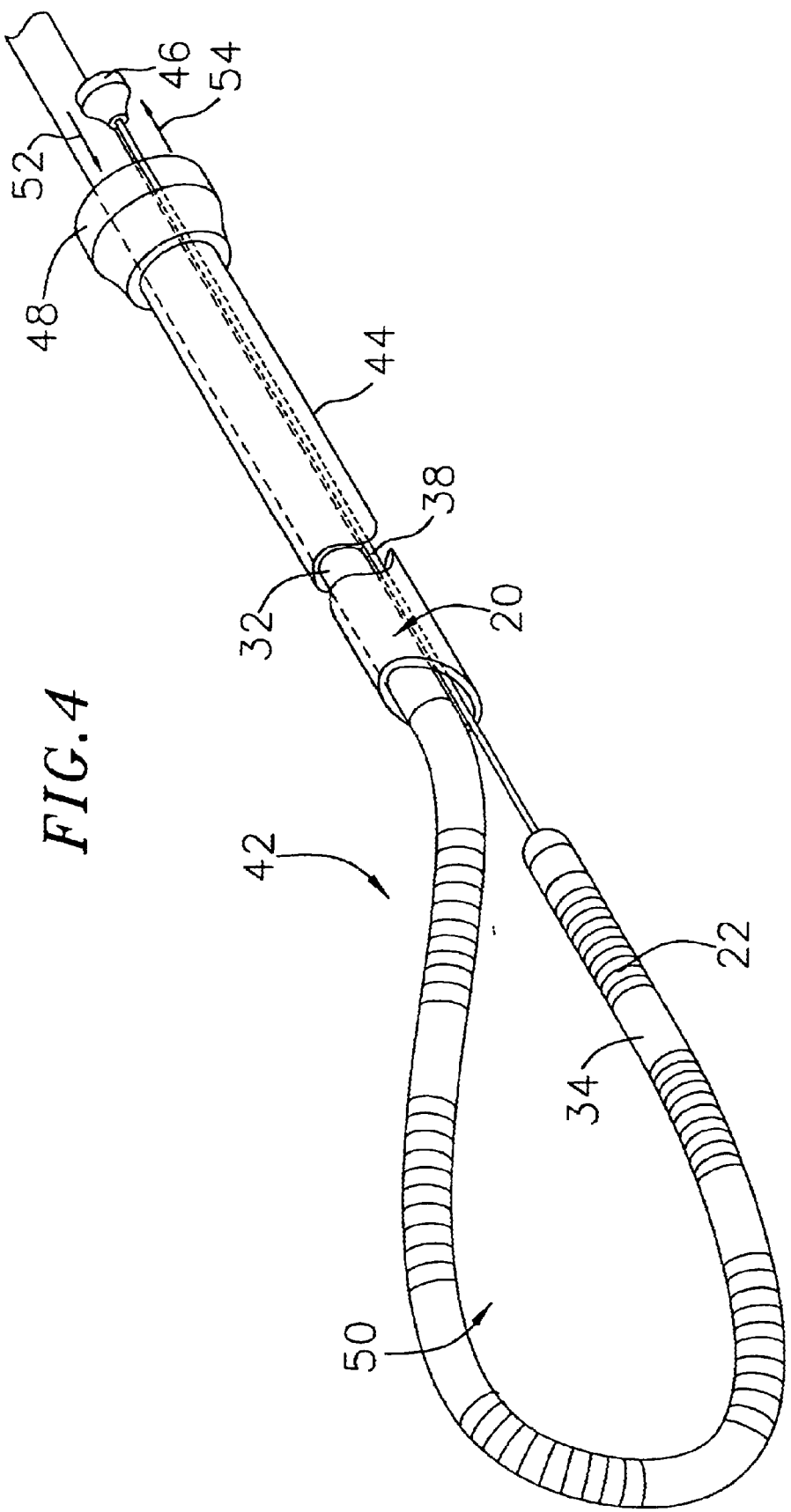
FIG. 4 is a perspective view of another probe including a loop structure in accordance with a preferred embodiment of a present invention.
Figure 13:
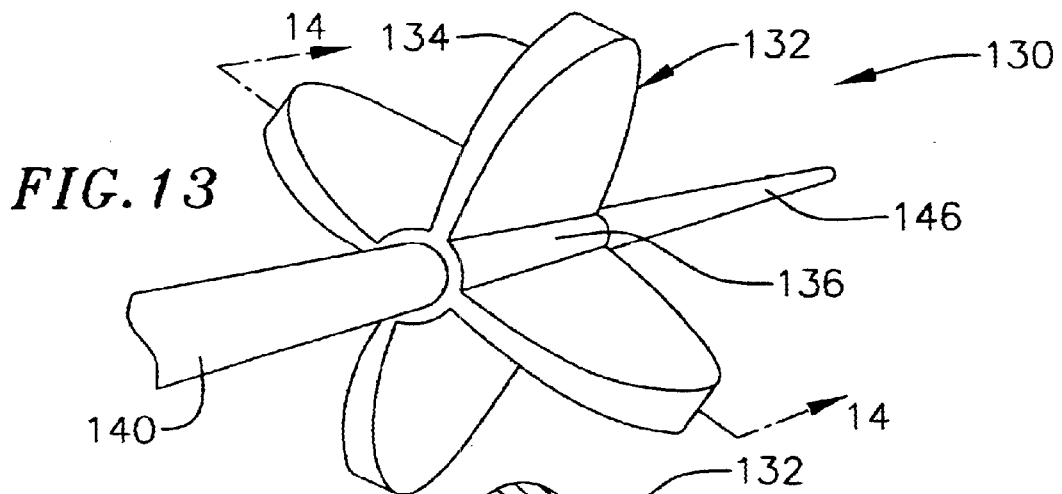
FIG. 13 is a perspective view of another probe including an inflatable-type expandable push structure in accordance with a preferred embodiment of a present invention.
Figure 14:
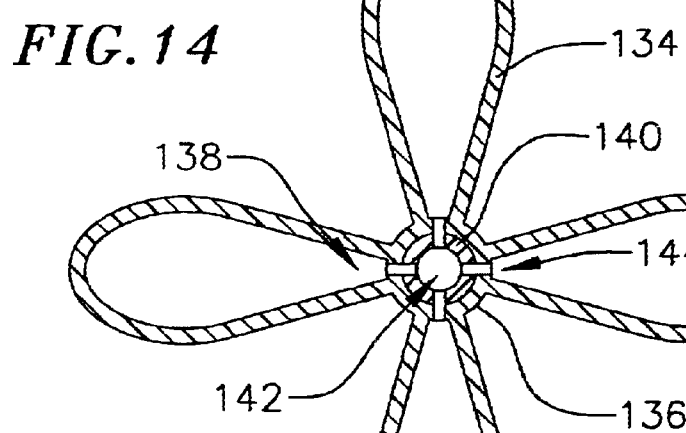
FIG. 14 is a section view taken along line 14—14 in FIG. 13.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Introduction
II. Apparatus Including Probes Having Loop Structures and Probes Having Expandable Push Structures
III. Loop Structures
IV. Basket-Type Expandable Push Structures
V. Inflatable-Type Expandable Push Structure
VI. Sheaths Including Expandable Push Structures
VII. Electrodes, Temperature Sensing and Power Control The section titles and overall organization of the present detailed description are for the purpose of convenience only and are not intended to limit the present inventions.

I. Introduction

The present inventions may be used within body lumens, chambers or cavities for diagnostic or therapeutic purposes in those instances where access to interior bodily regions is obtained through, for example, the vascular system or alimentary canal and without complex invasive surgical procedures. For example, the inventions herein have application in the diagnosis and treatment of arrhythmia conditions within the heart. The inventions herein also have application in the diagnosis or treatment of ailments of the gastrointestinal tract, prostrate, brain, gall bladder, uterus, and other regions of the body.

With regard to the treatment of conditions within the heart, the present inventions are designed to produce intimate tissue contact with target substrates associated with various arrhythmias, namely atrial fibrillation, atrial flutter, and ventricular tachycardia. For example, apparatus in accordance with a present invention, which may include diagnostic and/or soft tissue coagulation electrodes, can be used to create lesions within or around the pulmonary vein to treat-ectopic atrial fibrillation.

The inventions are also adaptable for use with probes other than catheter-based probes. For example, the inventions disclosed herein may be embodied in hand held surgical devices (or "surgical probes"). The distal end of a surgical probe may be placed directly in contact with the targeted tissue area by a physician during a surgical procedure, such as open heart surgery. Here, access may be obtained by way of a thoracotomy, median sternotomy, or thoracostomy. Exemplary surgical probes are disclosed in co-pending U.S. application Ser. No. 09/072,872, filed May 5, 1998, and entitled "Surgical Methods and Apparatus for Positioning a Diagnostic or Therapeutic Element Within the Body."

Surgical probes in accordance with the present inventions preferably include a handle, a relatively short shaft, and one of the distal assemblies described hereafter in the catheter context. Preferably, the length of the shaft is about 4 inches to about 18 inches. This is relatively short in comparison to the portion of a catheter body that is inserted into the patient (typically from 23 to 55 inches in length) and the additional body portion that remains outside the patient. The shaft is also relatively stiff. In other words, the shaft is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial.

II. Apparatus Including Probes Having Loop Structures and Probes Having Expandable Push Structures As illustrated for example in FIG. 1, an apparatus 10 in accordance with a preferred embodiment of a present invention includes a probe 12 having a loop structure 14 and a probe 16 having an expandable push structure 18. The exemplary loop structure 14, which is supported on the distal end of a catheter body 20, supports one or more diagnostic or therapeutic elements (collectively referred to as "operative elements") such as, for example, a plurality of spaced electrodes 22. The exemplary expandable push structure 18, which is supported near the distal end of a catheter body 24, is a basket structure consisting of a plurality of flexible splines 26. The portion of the catheter body 24 distal of the push structure 18 forms an anchor 28.

The expandable push structure 18 may be used to push the loop structure 14 against a tissue region, such as the pulmonary vein region, in order to achieve the desired level of contact between the electrodes 22 and the tissue. More specifically, the push structure 18 may be urged distally from the position illustrated in FIG. 1 so that the splines 26 engage the loop structure 14 and urge the loop structure against the tissue. The anchor 28 will preferably pass through the loop structure 14 to center the push structure 18 relative to the loop structure. The anchor will also center the push structure 18 and loop structure 14 relative to the pulmonary vein or other body orifice, which makes it easier to position the present apparatus 10 than conventional loop supporting devices.

The probes 12 and 16 may be separately directed to the anatomical region of interest, such as the left atria, and then positioned relative to one another in the manner illustrated for example in FIGS. 1 and 12A. A transseptal technique may be used to direct two separate probes through two separate sheaths (note FIG. 12A) from the right atria, through the fossa ovalis and into the left atria. One puncture may be made for each of the probes. Alternatively, given the elasticity of the membranous portion of the atrial septum, a single puncture may be made. Once one of the probes has been inserted through the puncture, the other probe can be wedged into the left atria between the inserted probe and the perimeter of the puncture. Transseptal techniques are especially useful in combination with probes having inflatable-type expandable push structures, such as those illustrated in FIGS. 10A–14.

When appropriate, another method is to arrange the probes 12 and 16 in the manner illustrated in FIG. 2 prior to inserting the apparatus 10 into a common sheath 30. Such a prearrangement of the probes 12 and 16 will result in the anchor 28 already being threaded through the loop structure 14 when the apparatus 10 exits the distal end of the sheath 30, thereby eliminating the need to thread the anchor through the loop structure at the anatomical region of interest. The exemplary sheath 30 should be lubricious to reduce friction during movement of the probes 12 and 16. The proximal portion of the sheath 30 is preferably a Pebax® and stainless steel braid composite and the distal portion is a more flexible material, such as unbraided Pebax®. An introducer sheath, such as those used in combination with conventional basket catheters, may be used when introducing the probes 12 and 16 into the sheath 30.

A wide variety of probes, loop structures, push structures, operative elements and combinations thereof may be incorporated into the apparatus 10. Additional details concerning the above-described and other probes, loop structures, push structures and operative elements is provided in the following sections of the Specification. The apparatus 10 may include all combinations of the probes, loop structures, push structures and operative elements.

III. Loop Structures

A number of exemplary catheter probes and loop structures are described below with reference to FIGS. 3A–6. Each may be used in combination with a probe including a push structure, such as those described below with reference to FIGS. 7–15, in the manner illustrated in FIGS. 1, 2 and 12A. The loops structures may also be used in combination with a sheath including a push structure, such as those described below with reference to FIGS. 16–24, in the manner illustrated in FIG. 17.

As illustrated for example in FIGS. 3A–3C, the probe 12 is preferably a catheter probe that includes a hollow, flexible catheter body 20 formed from two tubular parts, or members. The proximal member 32 is relatively long and is attached to a handle 33, while the distal member 34, which is relatively short, carries the plurality of spaced electrodes 22 or other operative elements. The proximal member 32 is typically formed from a biocompatible thermoplastic material, such as a Pebax® material (polyether block amide) and stainless steel braid composite, which has good torque transmission properties and, in some implementations, an elongate guide coil (not shown) may also be provided within the proximal member. The distal member 34 is typically formed from a softer, more flexible biocompatible thermoplastic material such as unbraided Pebax® material, polyethylene, or polyurethane. The proximal and distal members are preferably either bonded together with an overlapping thermal bond or adhesive bonded together end to end over a sleeve in what is referred to as a "butt bond."

The distal portion of the proximal member 32 includes a pre-shaped curved portion (or elbow) 36. Although other curvatures may be used, the curved portion 36 in the illustrated embodiment is a ninety degree downward (in the illustrated orientation) curve with a radius of about 0.5 inch. This results in an loop structure 14 that is out of plane with the remainder of the catheter.

The preset curvature may be accomplished in a variety of manners. Preferably, the curved portion 36 is preset through the use of a thermal forming technique (100° C. for 1 hour). The preset curvature may also be accomplished through the use of a pre-shaped spring member (not shown) formed from Nitinol® or 17-7 stainless steel that is positioned within the proximal member 32 and anchored where the proximal and distal members 32 and 34 are bonded to one another. Such a spring member would preferably be rectangular in cross-section and have a nominal radius of about 0.5 inch.

The exemplary catheter probe 12 illustrated in FIGS. 3A–3C also includes a pull wire 38 that is fixedly mounted within the distal region of the distal member 34, preferably in the manner illustrated in U.S. Pat. No. 5,910,129. The exemplary pull wire 38 is a flexible, inert cable constructed from strands of metal wire material, such as Nitinol® or 17-7 stainless steel, that is about 0.012 inch to about 0.025 inch in diameter. Alternatively, the pull wire 38 may be formed from a flexible, inert stranded or molded plastic material. The pull wire 38 is also preferably round in cross-section, although other cross-sectional configurations can be used. The pull wire 38 extends into the catheter body 20 through an aperture 40 formed in the proximal member 32 and extends to the proximal end of the catheter body where it is connected to a slide device 35 on the handle 33. The application of tension to the pull wire 38 pulls the distal member 34 into the loop illustrated in FIG. 3A.

Instead of the pull wire arrangement illustrated in FIG. 3A, a loop may be created through the use of a core wire (not shown) that is positioned within the distal member 34 and heat set into a loop configuration. The core wire is relatively flexible at body temperature that will assume a linear shape when it is within the sheath 30. The core wire (and distal member 34) may be driven into a loop shape by heating the core wire through, for example, resistive heating. Electrical leads are connected to the ends of the core wire for this purpose. A suitable material for the core wire is a shape memory alloy, such as actuator-type Nitinol®, that has a transition temperature above body temperature (typically between about 55° C. and 70° C.).

The dimensions of the probe 12 may be varied to suit the intended application. In a probe intended for use in pulmonary vein applications, the diameter of the catheter body will be between about 1 mm and about 3 mm and the diameter of the loop structure 14 will be between about 1 cm and about 4 cm.

Additional information concerning the exemplary probe illustrated in FIG. 3A, as well as information concerning the use of heat activated shape memory materials, is contained in concurrently filed U.S. application Ser. No. 09/447,180, entitled "Loop Structures For Supporting Diagnostic And Therapeutic Elements In Contact With Body Tissue," which is incorporated herein by reference.

Another exemplary catheter probe with a loop structure in accordance with a preferred embodiment of a present invention is illustrated in FIG. 4. The probe, which is generally represented by reference numeral 42, is substantially similar to the probe illustrated in FIG. 3A and common structural elements are represented by common reference numerals. The probe 42 includes a catheter body 20 that consists of a relatively long proximal member 32 that is connected to a handle (not shown) and a relatively short, flexible distal member 34 that carries the plurality of spaced electrodes 22 or other operative elements. The catheter probe also includes a pull wire 38 that is fixedly mounted within the distal region of the distal member 34. Here, however, the probe 42 includes a sheath 44 and the pull wire 38 extends into the sheath. The proximal end of the pull wire 38 extends outwardly from the proximal end of the sheath 44 is secured to a pull wire handle 46. Similarly, the proximal end of the sheath 44 is provided with a raised gripping surface 48.

The exemplary sheath 44 is preferably formed from a material having a greater inherent stiffness than the catheter body 20. Preferably, the sheath material is relatively thin (about 0.013 inch) and lubricious. One example of a suitable material is polytetrafluoroethylene (PTFE), preferably with a lubricious coating. Additional stiffness can be imparted by lining the sheath 44 with braided PEBAX® material.

The catheter probe 42, including the sheath 44, will preferably be inserted into a patient through the sheath 30 with a probe including an expandable push structure in the manner illustrated for example in FIG. 2. Of course, the two probes may also be inserted separately. In either case, a loop structure 50 may be created by holding the pull wire handle 46 stationary and advancing the catheter body 20 through the sheath 44 (arrow 52). Once the loop structure 50 has been formed, the physician can pull the pull wire 38 (arrow 54) to decrease its exposed length beyond the distal end of the sheath 44. Further adjustments to the loop structure 50 may then be made by advancing or retracting the catheter body 20 relative to the sheath 44.

Additional information concerning the exemplary probe illustrated in FIG. 4 is contained in aforementioned U.S. Pat. No. 5,910,129. In an alternative embodiment, the pull wire 38 will be secured to the distal end of the sheath 44. Here, the loop structure will be deployed and adjusted by simply advancing and retracting the catheter body 20 relative to the sheath. Such a probe is also described in U.S. Pat. No. 5,910,129.

As illustrated for example in FIGS. 5A–5C, an exemplary probe 56 in accordance with a preferred embodiment of a present invention includes a catheter body 58 and a collapsible loop structure 60 that carries a plurality of spaced electrodes 22 or other operative elements. The proximal end of the catheter body 58 is secured to a handle (not shown). The loop structure 60 consists of an annular tubular body 62 that defines a closed loop and an inner loop shaped center support (not shown). The annular tubular body 62 may be formed from biocompatible polymer material such as Pebax® or Nylon®. The center support is preferably formed from stranded Nitinol® that is held together by a crimped hypotube. The stranded Nitinol® structure is covered with a tube formed from Pebax® or other suitable material and the edges of the tube are bonded to the stranded Nitinol® structure with an adhesive.

The loop structure 60 is supported on the distal end of the catheter body 58 by a support assembly 57 that allows the loop structure to pivot relative to the catheter body. Referring more specifically to FIG. 5C, the support assembly 57 includes a first tubular member 59 with an opening 61 and a second tubular member 63 connected to the first tubular member such that the lumen of the second tubular member is aligned with the opening. The loop structure 60 passes through the first tubular member 59. A third tubular member 65 is secured to, and extends beyond the proximal end of, the first tubular member 59. The tubular members 59, 63 and 65 are preferably Nitinol® or stainless steel hypotubes that are soldered to one another. The third tubular member is inserted into the catheter body 58 and then secured thereto with adhesive, welds, or other suitable devices.

The annular tubular body 62 includes an aperture 64 through which conductor wires (not shown) for the electrodes 22 and temperature sensors (discussed below with reference to FIGS. 3B and 3C) on the loop structure 60 pass from the lumen of the catheter body 58 into the loop structure. The conductor wires, which may be housed in a flexible insulative structure, pass between the center support and the inner surface of the annular tubular body 62.

The exemplary probe 56 may be inserted into a patient through the sheath 30 along with a probe including an expandable push structure in the manner illustrated for example in FIG. 2. In those instances where the probes are to be inserted separately, a sheath 66 that is sufficiently stiff to collapse the loop structure 60 may be provided.

Another exemplary probe in accordance with a preferred embodiment of a present invention is illustrated in FIG. 6 and generally represented by reference numeral 68. Here too, a loop structure 60, consisting of an annular tubular body 62 formed from biocompatible polymer material such as Pebax® or Nylon® and an inner loop shaped center support (not shown), supports a plurality of electrodes 22 or other operative elements. The loop structure 60 is supported on a catheter body 70 that includes a proximal portion secured to a handle (not shown) and a pre-shaped curved distal portion 72 with a u-shaped bend. The loop structure 60 is secured to the distal end of the curved distal portion 72 by a support assembly 57 and is arranged such that it lies in a plane that is perpendicular (or nearly perpendicular) to the longitudinal axis of the catheter body 70.

IV. Basket-Type Expandable Push Structures

A number of exemplary basket-type expandable push structures are described below with reference to FIGS. 1, 2 and 7–9. Each may be used in combination with probes having loop structures, such as those described above with reference to FIGS. 3A–6, in the manner illustrated in FIGS. 1, 2 and 12A. One advantage of basket-type expandable push structures is that they will not occlude the flow of fluid through an orifice (such as blood through the pulmonary vein) when the push structure is pressing the loop structure against the tissue in or around the orifice.

The expandable push structure 18 on the exemplary probe 16 illustrated in FIGS. 1 and 2 is a basket structure consisting of a plurality of flexible splines 26. The splines 26 formed from a resilient, biologically inert material such as Nitinol® metal, stainless steel or silicone rubber. Base members 74 and 76 mount the splines on the catheter body 24 in a resilient, pretensed, radially expanded condition. The splines 26 will deform into the shape illustrated in FIG. 2 when the basket structure 18 is inserted into the sheath 30. The catheter body 24 is preferably formed from a biocompatible thermoplastic material, such as Pebax® and stainless steel braid composite. The proximal end of the catheter body may be secured to handle (not shown). The basket structure 18 is substantially similar to that of the Constellation® mapping basket manufactured by EP Technologies, Inc., although it lacks the electrodes and signal wires associated with mapping baskets.

The exemplary basket-type push structure 18 illustrated in FIGS. 1 and 2 is ellipsoid in shape. Other shapes may also be employed. For example, the exemplary probe 78 illustrated in FIG. 7 includes a basket structure 80 formed from splines 82 that have a slightly different pretensed shape than those illustrated in FIG. 1. The mid-portions of the splines 82 are relatively flat and the longitudinal ends are bowed in the proximal and distal directions. This gives the basket structure 80 a shape similar to a spheroid. Another exemplary probe, which is generally represented by reference numeral 84, is illustrated in FIG. 8. Here, the basket 86 includes a plurality of splines 88 that are shaped such that the basket has a conical portion 90 and a flared portion 92. Such a configuration is especially useful for centering the loop structure and maintaining tissue contact. The exemplary probe 94 illustrated in FIG. 9 includes a basket structure 96 with still another shape. The splines 98 in the basket structure 96 are shaped such that the basket structure has a distally facing funnel shape. This configuration is useful for insuring tissue contact. It should be noted that the illustrated and described shapes are merely examples of preferred shapes and that any suitable shape may be employed.

Each of the exemplary basket structures illustrated in FIGS. 1, 2 and 7–9 includes four splines that are symmetrically spaced about the longitudinal axis of the probes. Nevertheless, the number of splines may be adjusted, and the splines may be arranged asymmetrically, as applications require.

The maximum diameter (or width in a non-circular cross-section) of the basket-type push structures should be slightly larger than that of the loop structure with which it is used. In a pulmonary vein application, for example, the maximum diameter should be between about 1.5 cm and about 4.5 cm.

The exemplary probes illustrated in FIGS. 1, 2 and 7–9 include anchors 28 that center the push structures relative to the loop structures used therewith and also center the push structures and loop structures relative to the pulmonary vein or other body orifice. The anchors 28 may also be used to support diagnostic and/or therapeutic devices. As illustrated for example in FIG. 7, the anchor 28 may be used to support a relatively small mapping basket 100 that can, for example, map the pulmonary vein after a coagulation procedure to determine whether a curative lesion has been formed. This eliminates the need to remove the device being used to create the lesion, such as a loop structure, so that a diagnostic device can be appropriately positioned. The length of the anchor 28 will vary according to the intended application. In a pulmonary vein application, for example, the anchor 28 will be about 2 cm to about 5 cm in length.

Although other configurations may be employed, the exemplary basket 100 illustrated in FIG. 7 includes four splines 102 and each spline supports a pair of electrodes 104. Although somewhat smaller (about 30 mm in diameter), such a basket would be similar to the Constellation® mapping basket manufactured by EP Technologies, Inc. As illustrated for example in FIG. 8, a single electrode 106 (or bipolar electrode pair) may instead be carried by the anchors 28 for mapping and other diagnostic or therapeutic purposes. The electrode(s) 106 is preferably radiopaque for fluoroscopic imaging purposes. The electrodes 104 and 106 are connected to individual conductor wires (not shown) that extend through a lumen to the proximal end of the catheter body in conventional fashion.

A conventional catheter handle 108 (FIG. 7) may be used in conjunction with any of the exemplary probes that support basket-type expandable push structures. In those instances where the probe includes a diagnostic or therapeutic device, the conductor wires therefrom may be connected to a PC board within handle that can mate with a suitable electrical connector via a connector port 110.

V. Inflatable-Type Expandable Push Structures

A number of exemplary inflatable-type expandable push structures are described below with reference to FIGS. 10A–14. Each may be used in combination with probes including loop structures, such as those described above with reference to FIGS. 3A–6, in the manner described below with reference to FIG. 12B.

As illustrated for example in FIGS. 10A and 11, an exemplary probe 112 in accordance with a preferred embodiment of a present invention includes a flexible catheter body 114 that may be formed from a biocompatible thermoplastic material such as braided or unbraided Pebax® (polyether block amide), polyethylene, or polyurethane. The proximal end of the catheter body 114 is secured to a handle 116. An inflatable (and deflatable) type expandable push structure 118 is bonded to and disposed around the catheter body 114 near the distal end thereof. The inflatable push structure 118 can be inflated with isotonic saline solution or other biocompatible fluids. The fluid is supplied under pressure to the catheter body 114 through an infusion/ventilation port 120. The pressurized fluid travels to and from the inflatable push structure 118 through a fluid lumen 122 in the catheter body 114 and an aperture 124 located within the inflatable push structure. Pressure is maintained to maintain the inflatable push structure 118 in the expanded orientation illustrated in FIG. 10A. The pressure should be relatively low (less than 5 psi) and will vary in accordance with the desired level of inflation, strength of materials used and the desired degree of flexibility. The fluid may be removed from the inflatable push structure 118 by applying a suction force to the infusion/ventilation port 120.

For applications associated with the creation of lesions in or around the pulmonary vein, the exemplary inflatable push structure 118 is preferably located about 3 cm to about 5 cm from the distal tip of the catheter body 114 and the diameter (or width in a non-circular cross-section) is between about 2.3 mm and 5 mm in the collapsed state and between about 1.5 cm and about 4.5 cm in the inflated state. Suitable materials for the inflatable push structure 118 include relatively elastic biocompatible materials that can withstand the heat generated by the electrodes on a loop structure during a coagulation procedure. Suitable materials include silicone, Pebax®, C-Flex® and Latex®.

Probes with inflatable-type expandable push structures will preferably, although not necessarily, be advanced to the target region though a sheath. As illustrated for example in FIGS. 12A and 12B, a probe 112" may be configured such that it can be advanced over a guidewire 121 as well as through a sheath 123. Here, the catheter body 114' will include a central guidewire lumen 126 and an offset fluid lumen 122'. The central guidewire lumen 126, which may be incorporated into any of the expandable push structures disclosed in the present application, has a variety of other uses. For example, a steering device, such as a stylet or steerable catheter, may also be inserted into the guidewire lumen 126 and used to steer the probe to the pulmonary vein or other target tissue region. A mapping catheter may also be inserted through the guidewire lumen 126. The central guide wire lumen 126 may be used to inject contrast material into a target tissue region, such as the pulmonary vein, so that an outline image of the region can be visualized during fluoroscopy.

Much like the exemplary probes with basket-type push structures illustrated in FIGS. 1, 2 and 7–9, the exemplary probes illustrated in FIGS. 10A–12B include an anchor 128 located distally of the inflatable push structure 118. The anchor 128 may be used to center the push structure relative to the loop structures used therewith and to center the push structure and loop structures relative to the pulmonary vein or other body orifice. The anchor 128 may also be used to support diagnostic and/or therapeutic devices, such as the relatively small mapping basket 100 (probe 112 in FIG. 10A), a single electrode 106 (probe 112' in FIG. 10B), or a pair of electrodes 106 (probe 112" in FIG. 12A), which may be used before and after coagulation procedures. Here, the catheter body 114 will be provided with a wire lumen 125 for conductor wires 127 and the handle 116, which is illustrated in FIG. 10A, will be provided with a PC board and a connector port 129.

As illustrated for example in FIG. 12A, the inflatable push structure 118 may be used to urge the loop structure 14 and electrodes 22 against the ostium of a pulmonary vein. The inflatable push structure 118 will conform to and deform around the loop structure 14 as the loop structure is pressed against the tissue, thereby thermally and electrically insulating the electrodes 22 from circulating blood. This reduces convective cooling and system power requirements because the amount of heat that flows into the blood from the tissue and electrodes 22 is reduced, as is the amount of power delivered directly into the blood. In in vitro testing, for example, the temperature-controlled power required to coagulate tissue with a saline filled Latex® inflatable push structure pressed over the electrodes was about ⅓ of the power required to coagulate tissue without the inflatable push structure. The use of the inflatable push structure 118 also increases the accuracy of peak tissue temperature measurements. The difference between the hottest tissue temperature and the temperatures sensed at the electrodes is reduced because temperature gradients near the electrodes are reduced.

The exemplary inflatable push structure 118 has a generally spherical shape. Other shapes may also be employed. As illustrated for example in FIGS. 13–15, a probe 130 in accordance with a preferred embodiment of a present invention includes a clover leaf-shaped inflatable push structure 132 with four radially extending members 134 mounted on a cylindrical base 136. Each of the radially extending members includes an inlet 138. The cylindrical base 136 supports the push structure 132 on a catheter body 140 having a central fluid lumen 142 and four apertures 144 that are aligned with the inlets 138. The catheter body 140 also includes an anchor 146 located distally of the push structure 132.

Figure 15:
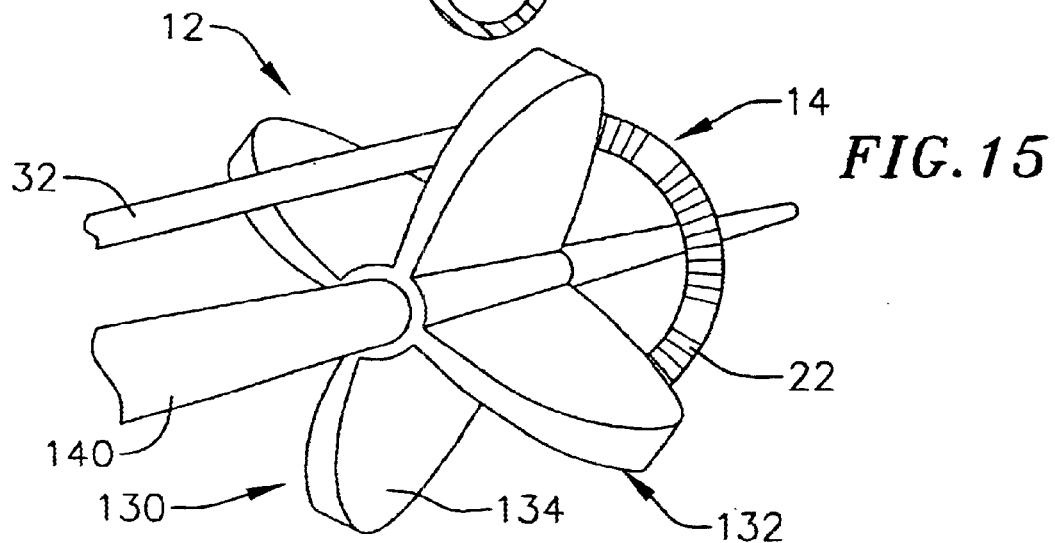
FIG. 15 is a perspective view of the probe illustrated in FIG. 13 being used in combination with a probe including a loop structure.

The clover leaf shape allows the probe 130 to be positioned relative to a probe that supports a loop structure, such as the probe 12 described above with reference to FIG. 3A, in the manner illustrated in FIG. 15. This results in an overall apparatus (i.e. one that includes a probe with a loop structure and a probe with a push structure) that is more compact than that achieved with the inflatable structure illustrated in FIG. 10A. The clover leaf shape is also advantageous in that the push structure will not occlude the flow of fluid through an orifice (such as blood through the pulmonary vein) when the push structure is pressing the loop structure against the tissue in or around the orifice.

Still other shapes, such as a tear drop shape, a cylindrical shape, or a prolate ellipsoid, may also be employed as applications require. It should be noted that the illustrated and described shapes are merely examples of preferred shapes and that any suitable shape may be employed.

VI. Sheaths Including Expandable Push Structures

As discussed above with reference to FIG. 2, probes including loop structures may be advanced through a sheath to a target tissue region. An expandable structure may then be used to urge the loop structure into contact with the tissue. In accordance with a preferred embodiment of a present invention, the expandable push structure is a part of the sheath itself, as opposed to being mounted on a separate probe that travels through the sheath.

Figure 16:
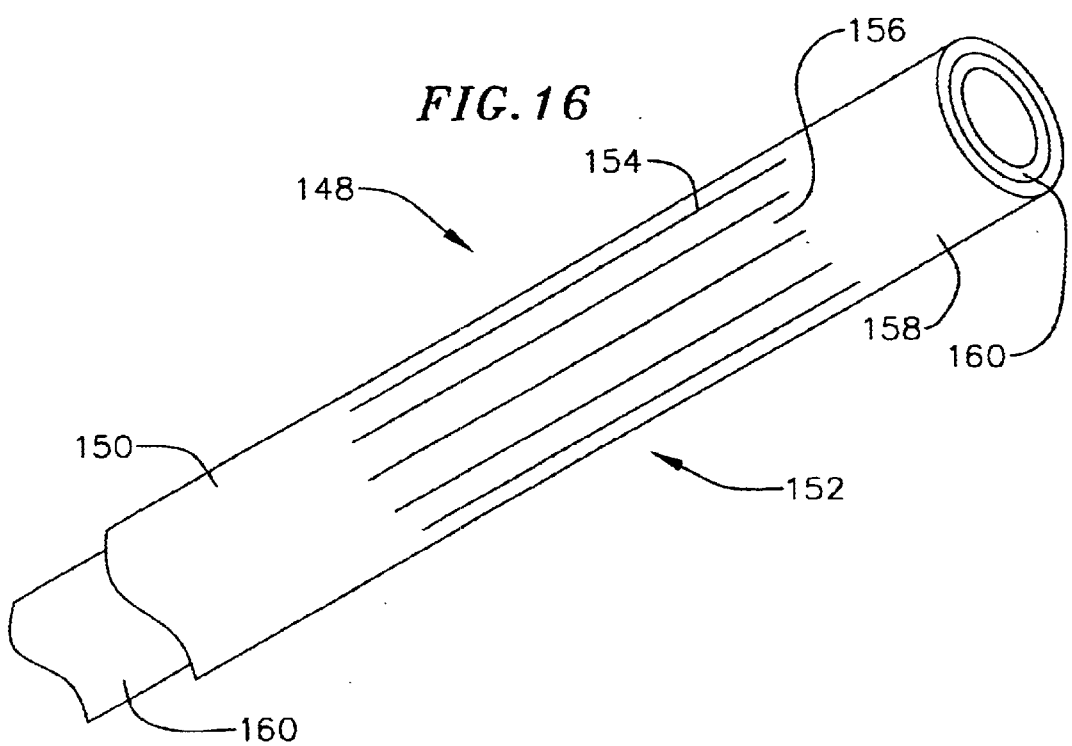
FIG. 16 is a perspective view of a sheath including an expandable push structure in an unexpanded state in accordance with a preferred embodiment of a present invention.
Figure 17:
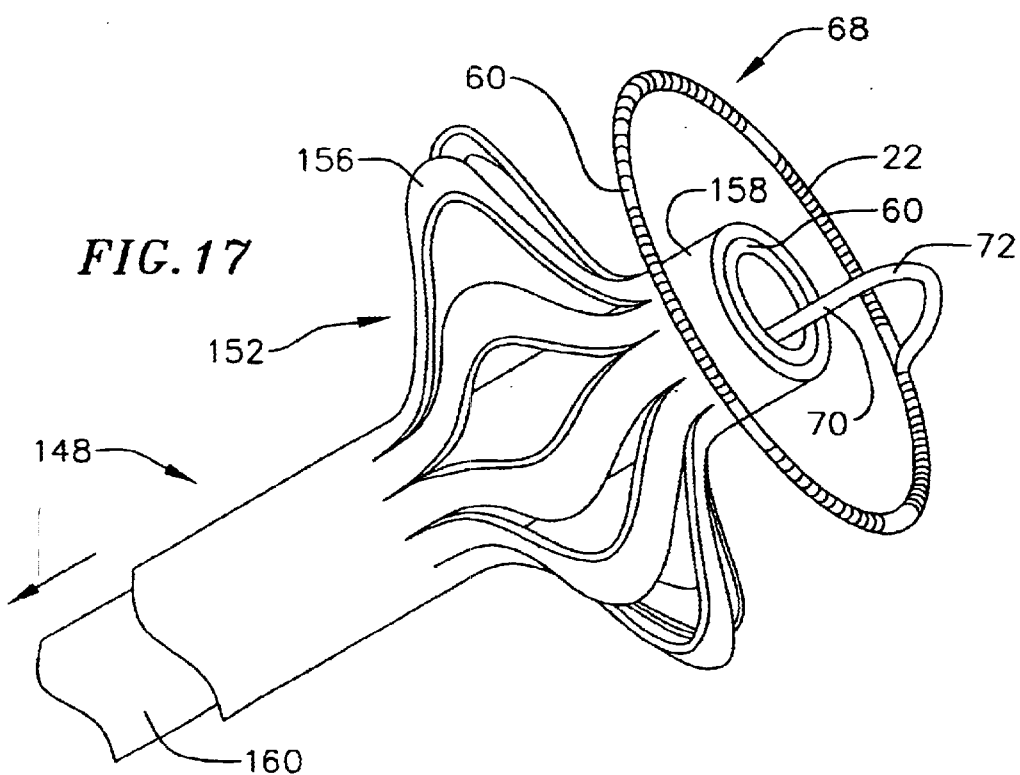
FIG. 17 is a perspective view of the sheath illustrated in FIG. 16 with the expandable push structure in an expanded state being used in combination with a probe including a loop structure.
Figure 22:
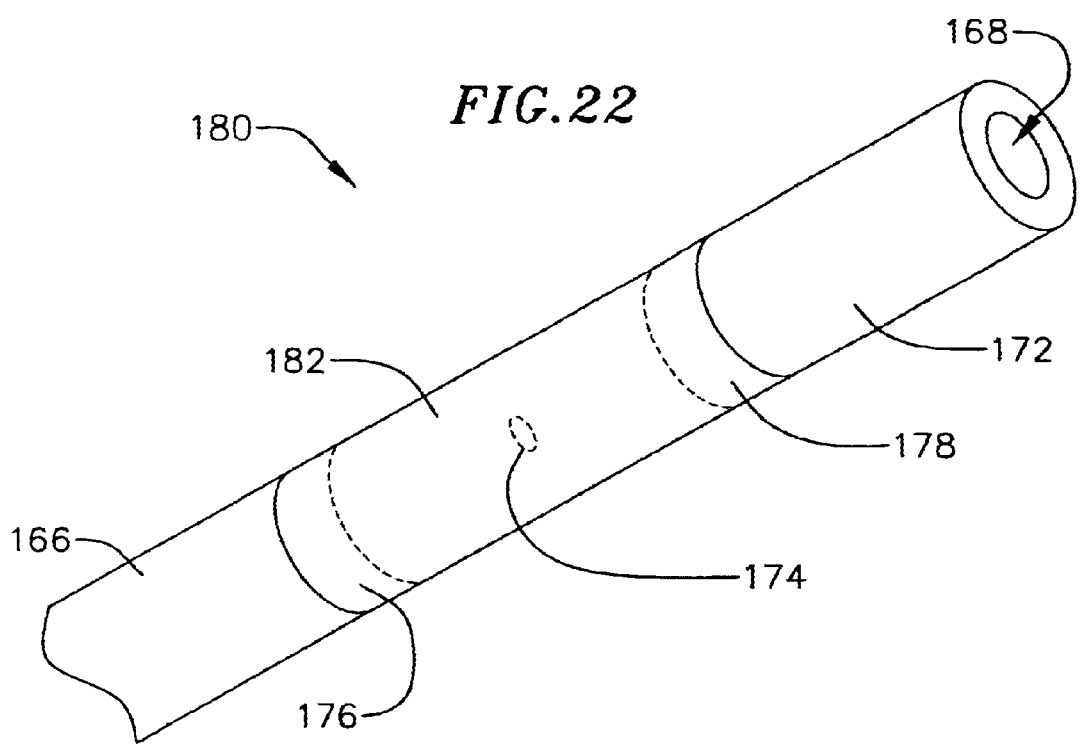
FIG. 22 is a partial perspective view of still another sheath including an inflatable-type expandable push structure in an unexpanded state in accordance with a preferred embodiment of a present invention.
Figure 23:
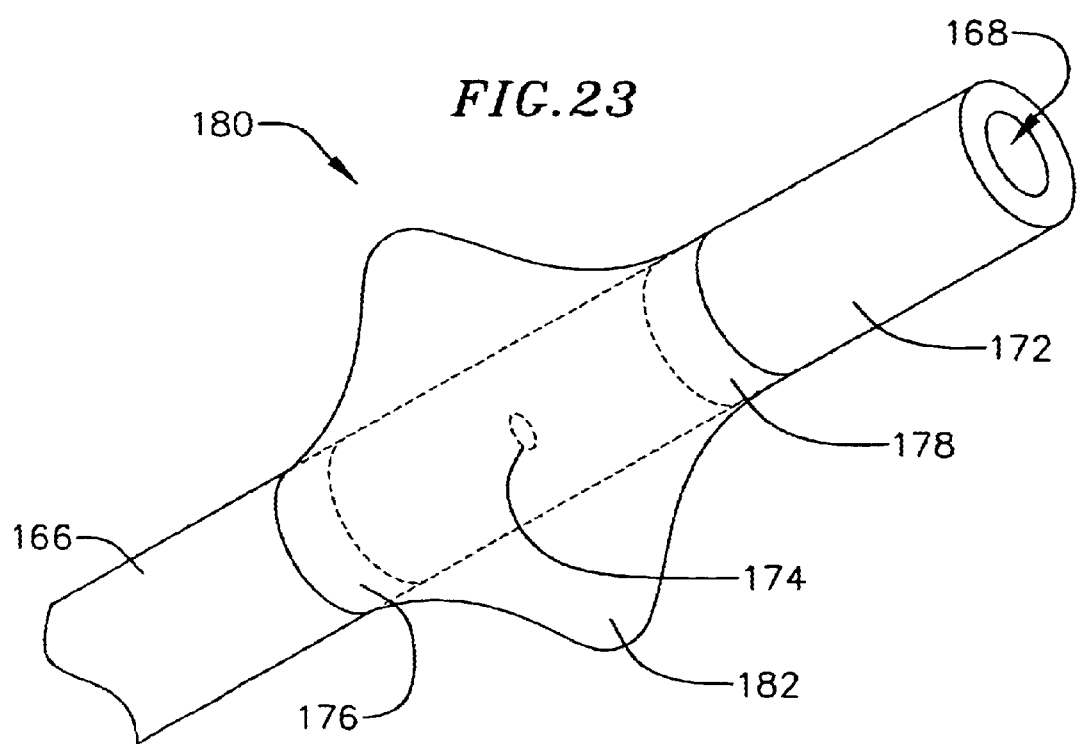
FIG. 23 is a partial perspective view of the sheath illustrated in FIG. 22 with the push structure in an expanded state.

As illustrated for example in FIGS. 16 and 17, a sheath 148 in accordance with a preferred embodiment of a present invention includes a main body portion 150 that extends to the proximal end of the sheath and occupies the substantial majority thereof as well as an expandable portion 152. The expandable portion 152 is formed by a plurality of slits 154 that divide the expandable portion into a plurality of arms 156 that form the push structure. Such a push structure will not occlude the flow of fluid through an orifice (such as blood through the pulmonary vein) when the push structure is pressing the loop structure against the tissue in or around the orifice. The exemplary sheath 148 also includes an anchor 158.

The expandable portion 152 of the exemplary sheath 148 may be urged between the collapsed state illustrated in FIG. 16 and the expanded state illustrated in FIG. 17 by moving the main body portion 150 and the anchor 158 relative to one another. For example, the anchor 158 may be held in place while the main body portion 150 is moved in the distal direction or, alternatively, the anchor may be moved in the proximal direction while the main body portion is held in place (as shown). An inner tubular body 160, which is connected to the anchor 158, allows the physician to either hold the anchor in place or move it in the proximal direction. The distal portion of the inner tubular body 160 is secured through the use of adhesive or other suitable bonding techniques to the anchor 158. No slots are formed in the inner tubular body 160. Alternatively, the inner tubular body 160 may be replaced by an anchor ring embedded in the anchor 158 and a pull wire or stylet that is connected to the anchor ring and extends to the proximal end of the main body portion 150. The stylet should be stiff enough to allow the physician to push the anchor 158 in the distal direction.

Once the expandable portion 152 has been brought into the expanded state illustrated in FIG. 17, it may be used to urge an electrode supporting loop structure, such as the loop structure 60 on the exemplary probe 68, into contact with tissue.

The exemplary sheath 148 is preferably formed from a lubricious tubular body consisting of a Pebax® and stainless steel braid composite or unbraided Pebax®. The inner tubular body 160 may be formed from similar materials. The arms 156 may, if applications require, include reinforcing structures such as splines formed from Nitinol® and/or other resilient materials. The arms 156 may also include scoring, preferably near the midpoints thereof, to insure proper bending. The diameter of the sheath and the expandable portion 152 will vary according to application. In pulmonary vein applications, for example, the sheath is preferably between about 3.3 mm and about 6.2 mm in outer diameter and has an inner diameter of between about 2.6 mm and about 5.5 mm. The expanded diameter of the expandable portion 152 should be between about 1.5 cm and about 4.5 cm.

Turning to FIGS. 18–21, a sheath 162 in accordance with a preferred embodiment of a present invention is provided with an inflatable push structure 164 that is mounted near the distal end of a tubular body 166. The tubular body 166 includes a central lumen 168 for passage of a probe that supports a loop structure or other device, a fluid lumen 170, and a distal portion that defines an anchor 172. Fluid, such as water, isotonic saline solution, or other biocompatible fluids, is supplied under pressure to the fluid lumen 170 and enters the inflatable push structure 164 through an aperture 174 located within the inflatable push structure. Pressure is maintained to maintain the inflatable push structure 164 in the expanded orientation illustrated in FIGS. 19 and 20. The pressure should be relatively low (less than 5 psi) and will vary in accordance with the desired level of inflation, strength of materials used and the desired degree of flexibility. The fluid may be removed from the inflatable push structure 164 by applying a suction force to the fluid lumen 170.

The inflatable push structure 164 is secured to the tubular body 166 at bond regions 176 and 178 that are located inwardly from the proximal and distal ends of the push structure. As a result, the exemplary inflatable push structure 164 has a generally ellipso-toroidal shape. Alternatively, and as illustrated for example in FIGS. 22 and 23, a probe 180 in accordance with another preferred embodiment is provided with an inflatable push structure 182 having an outwardly flared middle portion and proximal and distal ends which are secured to the tubular body 166 by bond regions 176 and 178. Other shapes, such as a spherical shape, a tear drop shape, a cylindrical shape, a clover leaf shape or a prolate ellipsoid, may also be employed.

The tubular body 166 may be formed from a biocompatible thermoplastic material such as braided or unbraided Pebax® (polyether block amide), polyethylene, or polyurethane, and is preferably about 3.3 mm to about 6.2 mm in diameter. The inflatable push structures 164 and 182 may be formed from relatively elastic biocompatible materials, such as silicone or C-Flex®, that can withstand the heat generated by the electrodes on a loop structure during a coagulation procedure. The inflatable push structures 164 and 182 are also preferably located about 3 cm to about 5 cm from the distal tip of the tubular body 166. Their diameter (or width in a non-circular cross-section) is between about 2.3 mm and about 5 mm in the collapsed state and between about 15 mm and about 45 mm in the inflated state.

Figure 24:
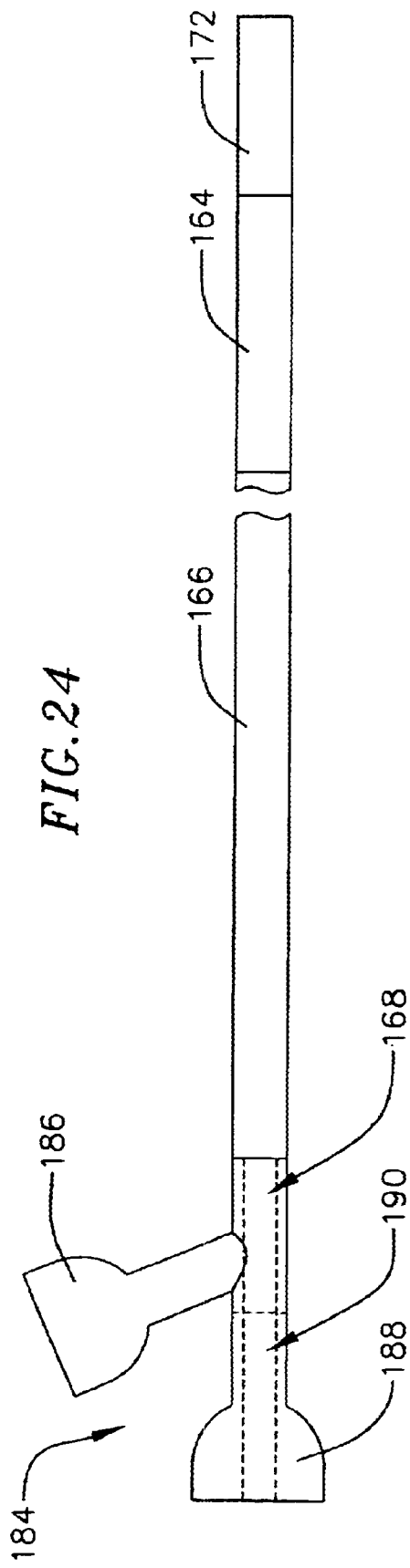
FIG. 24 is a side view of the sheath illustrated in FIG. 18 with a handle attached thereto.

As illustrated for example in FIG. 24, the exemplary sheaths illustrated in FIGS. 18–23 may be used in conjunction with a handle 184 with an infusion/ventilation port 186 that is operably connected to the fluid lumen 170. The handle 184 also includes a probe port 188 and a lumen 190 that are aligned with the central lumen 168 in the tubular body 166.

VII. Electrodes, Temperature Sensing and Power Control

In each of the exemplary loop structures illustrated in FIGS. 3A–6, the operative elements are a plurality of spaced electrodes 22. However, other operative elements, such as lumens for chemical ablation, laser arrays, ultrasonic transducers, microwave electrodes, and ohmically heated hot wires, and such devices may be substituted for the electrodes. Additionally, although electrodes and temperature sensors are discussed below in the context of the exemplary probe illustrated in FIGS. 3A–3C, the discussion is applicable to all of the loop structures disclosed herein.

The spaced electrodes 22 are preferably in the form of wound, spiral coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. A preferred coil electrode is disclosed in U.S. Pat. No. 5,797,905. The electrodes 22 are electrically coupled to individual wires 192 (FIG. 3B) to conduct coagulating energy to them. The wires are passed in conventional fashion through a lumen extending through the catheter body 20 into a PC board in the handle 33, where they are electrically coupled to a connector that is received in a port 194 on the handle. The connector plugs into a source of RF coagulation energy.

As an alternative, the electrodes may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

The flexible electrodes 22 are preferably about 4 mm to about 20 mm in length. In the preferred embodiment, the electrodes are 12.5 mm in length with 1 mm to 3 mm spacing, which will result in the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns.

The portion of the electrodes that are not intended to contact tissue (and be exposed to the blood pool) may be masked through a variety of techniques with a material that is preferably electrically and thermally insulating. This prevents the transmission of coagulation energy directly into the blood pool and directs the energy directly toward and into the tissue. It also prevents heat related damage to the push structures. For example, a layer of UV adhesive (or another adhesive) may be painted on preselected portions of the electrodes to insulate the portions of the electrodes not intended to contact tissue. Deposition techniques may also be implemented to position a conductive surface only on those portions of the assembly intended to contact tissue. Alternatively, a coating may be formed by dipping the electrodes in PTFE material.

The electrodes may be operated in a uni-polar mode, in which the soft tissue coagulation energy emitted by the electrodes is returned through an indifferent patch electrode (not shown) externally attached to the skin of the patient. Alternatively, the electrodes may be operated in a bi-polar mode, in which energy emitted by one or more electrodes is returned through other electrodes. The amount of power required to coagulate tissue ranges from 5 to 150 w.

As illustrated for example in FIG. 3C, a plurality of temperature sensors 196, such as thermocouples or thermistors, may be located on, under, abutting the longitudinal end edges of, or in between, the electrodes 22. Preferably, the temperature sensors 196 are located at the longitudinal edges of the electrodes 22 on the distally facing side of the loop structure 14. In some embodiments, a reference thermocouple may also be provided. For temperature control purposes, signals from the temperature sensors are transmitted to the source of coagulation energy by way of wires 198 (FIG. 3A) that are also connected to the aforementioned PC board in the handle.

Suitable temperature sensors and controllers which control power to electrodes based on a sensed temperature are disclosed in U.S. Pat. Nos. 5,456,682, 5,582,609 and 5,755,715.

The temperature sensors 196 are preferably located within a linear channel 200 that is formed in the distal member 34. The linear channel 200 insures that the temperature sensors 196 will directly face the tissue and be arranged in linear fashion. The illustrated arrangement results in more accurate temperature readings which, in turn, results in better temperature control. As such, the actual tissue temperature will more accurately correspond to the temperature set by the physician on the power control device, thereby providing the physician with better control of the lesion creation process and reducing the likelihood that embolic materials will be formed. Such a channel may be employed in conjunction with any of the electrode (or other operative element) supporting structures disclosed herein.

Finally, the electrodes 22 and temperature sensors 196 can include a porous material coating, which transmits coagulation energy through an electrified ionic medium. For example, as disclosed in U.S. application Ser. No. 08/879,343, filed Jun. 20, 1997, entitled "Surface Coatings For Catheters, Direct Contacting Diagnostic and Therapeutic Devices," electrodes and temperature sensors may be coated with regenerated cellulose, hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

Although the present inventions have been described in terms of the preferred embodiments above, numerous modifications and/or additions to the above-described preferred embodiments would be readily apparent to one skilled in the art. It is intended that the scope of the present inventions extends to all such modifications and/or additions and that the scope of the present inventions is limited solely by the claims set forth below.

We claim:

1. An apparatus, comprising:
    a first probe including a first probe body defining a proximal portion and a distal portion and a loop structure associated with the distal portion;
    at least one operative element associated with the loop structure; and
    a second probe including a second probe body defining a proximal portion and a distal portion and an expandable push structure associated with the distal portion.

2. An apparatus as claimed in claim 1, wherein at least one of the first and second probe bodies comprises a catheter body.

3. An apparatus as claimed in claim 1, wherein the first probe body defines a distal end and the loop structure is associated with the distal end of the first probe body.

4. An apparatus as claimed in claim 1, wherein the loop structure defines an opening having a width, the expandable push structure defines a maximum width and the maximum width of the expandable push structure is greater than the width of the opening.

5. An apparatus as claimed in claim 1, wherein the at least one operative element comprises a plurality of spaced electrodes.

6. An apparatus as claimed in claim 1, wherein the proximal portion of the first probe body is less flexible than the distal portion of the first probe body.

7. An apparatus as claimed in claim 1, wherein the first probe body defines a longitudinal axis and the loop structure defines a plane oriented at a non-zero angle to the longitudinal axis.

8. An apparatus as claimed in claim 7, wherein the plane is perpendicular to the longitudinal axis.

9. An apparatus as claimed in claim 1, wherein the first probe body defines a distal end and includes a pull wire extending distally from the distal end.

10. An apparatus as claimed in claim 9, wherein the first probe body defines an aperture located in spaced relation to the distal end and the pull wire extends into the aperture and to the proximal portion of the first probe body.

11. An apparatus as claimed in claim 9, wherein the first probe includes a sheath, the first probe body is located at least partially within the sheath and defines an exterior, and the pull wire extends into the sheath and to the proximal portion of the first probe body along the exterior.

12. An apparatus as claimed in claim 1, wherein the loop structure defines a closed loop.

13. An apparatus as claimed in claim 12, wherein the distal portion of the first probe body defines an aperture and the closed loop passes through the aperture.

14. An apparatus as claimed in claim 12, wherein the closed loop is fixedly secured to the distal portion of the first probe body.

15. An apparatus as claimed in claim 1, wherein the expandable push structure comprises a basket structure including a plurality of flexible splines.

16. An apparatus as claimed in claim 15, wherein second probe body defines a longitudinal axis and the splines are symmetrically spaced about the longitudinal axis.

17. An apparatus as claimed in claim 15, wherein the basket structure defines a generally ellipsoidal shape.

18. An apparatus as claimed in claim 15, wherein the basket structure defines a generally spheroidal shape.

19. An apparatus as claimed in claim 15, wherein the basket structure includes a conical portion and a flared portion.

20. An apparatus as claimed in claim 15, wherein the basket structure defines a funnel shape.

21. An apparatus as claimed in claim 1, wherein the expandable push structure comprises an inflatable structure.

22. An apparatus as claimed in claim 21, wherein the second probe includes an infusion lumen operatively connected to the inflatable structure.

23. An apparatus as claimed in claim 21, wherein the inflatable structure defines a spherical shape.

24. An apparatus as claimed in claim 21, wherein the inflatable structure includes a plurality of radially extending members.

25. An apparatus as claimed in claim 21, wherein the inflatable structure defines an ellipso-toroidal shape.

26. An apparatus as claimed in claim 1, wherein the second probe body defines a longitudinally extending lumen and a distal opening associated with the lumen.

27. An apparatus as claimed in claim 26, wherein the second probe body defines a distal end and the expandable push structure comprises a plurality of arms that bow outwardly when the proximal portion and distal end of the second probe body are moved closer together.

28. An apparatus as claimed in claim 26, wherein the expandable push structure comprises an inflatable push structure.

29. An apparatus as claimed in claim 1, wherein the second probe includes an anchor distal of the expandable push structure.

30. An apparatus as claimed in claim 29, further comprising:
    a diagnostic device carried by the anchor.

31. A sheath for use with a probe including at least one operative element, the sheath comprising:
    an elongate body defining a probe lumen, a proximal portion, a distal portion, a distal opening, and an anchor;
    an expandable push structure associated with the distal portion and proximal to the anchor; and
    a diagnostic device carried by the anchor.

32. A sheath for use with a probe including at least one operative element, the sheath comprising:
    an elongate body defining a probe lumen, a proximal portion, a distal portion, a distal end, and a distal opening; and
    a basket structure including a plurality of flexible splines, mounted on the distal portion in spaced relation to the distal end, for pushing the probe against tissue.

33. A sheath as claimed in claim 32, wherein elongate body defines a longitudinal axis and the splines are symmetrically spaced about the longitudinal axis.

34. A sheath for use with a probe including at least one operative element, the sheath comprising:
    an elongate body defining a probe lumen, a proximal portion, a distal portion, and a distal opening; and
    an inflatable push structure defining an ellipso-toroidal shape associated with the distal portion.

* * * * *